United States Patent
Parkinson

(10) Patent No.: US 11,867,780 B2
(45) Date of Patent: Jan. 9, 2024

(54) MRI MAGNET AND APPARATUS

(71) Applicant: VICTORIA LINK LIMITED, Wellington (NZ)

(72) Inventor: Benjamin John Parkinson, Lower Hutt (NZ)

(73) Assignee: VICTORIA LINK LIMITED, Wellington (NZ)

( * ) Notice: Subject to any disclaimer, the term of this patent is extended or adjusted under 35 U.S.C. 154(b) by 620 days.

(21) Appl. No.: 17/056,278

(22) PCT Filed: May 22, 2019

(86) PCT No.: PCT/NZ2019/050055
§ 371 (c)(1),
(2) Date: Nov. 17, 2020

(87) PCT Pub. No.: WO2019/245387
PCT Pub. Date: Dec. 26, 2019

(65) Prior Publication Data
US 2021/0190888 A1   Jun. 24, 2021

(30) Foreign Application Priority Data
Jun. 20, 2018 (AU) .............................. 2018902200

(51) Int. Cl.
*G01R 33/00* (2006.01)
*G01R 33/34* (2006.01)
(Continued)

(52) U.S. Cl.
CPC ...... *G01R 33/34023* (2013.01); *A61B 5/0042* (2013.01); *A61B 5/055* (2013.01); *A61B 5/70* (2013.01); *G01R 33/3804* (2013.01)

(58) Field of Classification Search
CPC .............................................. G01R 33/34023
See application file for complete search history.

(56) References Cited

U.S. PATENT DOCUMENTS 6,853,281 B1 * 2/2005 Kakugawa ......... G01R 33/3815
324/319
6,950,001 B2 * 9/2005 Kruip ................. G01R 33/3806
335/216
(Continued)

FOREIGN PATENT DOCUMENTS

WO   2010134006 A2   11/2010
WO   2013017139 A1    2/2013
(Continued)

OTHER PUBLICATIONS

International Search Report and Written Opinion dated Aug. 8, 2019 for corresponding PCT Application No. PCT/NZ2019/050055.

*Primary Examiner* — Joseph M Santos Rodriguez
(74) *Attorney, Agent, or Firm* — POLSINELLI PC

(57) ABSTRACT

An asymmetric magnet for use in performing MRI of a patient's head. The magnet has a patient end. The magnet provides an offset imaging volume (35) in a recess with an isocentre that is positioned closer to the patient end than an opposite end. The magnet has at least three groups of coils (44, 45, 46) in a generally tapering arrangement. The magnet also has an additional group of coils (47). A first group of coils (44) overlaps the additional group of coils (47), such that a bottom portion (47") of the additional group of coils (47) is positioned closer to the patient end of the magnet than a top portion (44') of the first group of coils (44).

20 Claims, 13 Drawing Sheets

(51) Int. Cl.
*A61B 5/00* (2006.01)
*A61B 5/055* (2006.01)
*G01R 33/38* (2006.01)

(56) References Cited

U.S. PATENT DOCUMENTS

| | | | |
|---|---|---|---|
| 7,304,478 B2 * | 12/2007 | Tsuda | G01R 33/3815 |
| | | | 324/322 |
| 7,449,888 B1 | 11/2008 | Malik et al. | |
| 2008/0097192 A1 | 4/2008 | Driemel | |
| 2014/0159727 A1 | 6/2014 | Lee et al. | |

FOREIGN PATENT DOCUMENTS

| | | |
|---|---|---|
| WO | 2015043612 A1 | 4/2015 |
| WO | 2018097862 A1 | 5/2018 |

\* cited by examiner

MRI MAGNET AND APPARATUS

CROSS-REFERENCE TO RELATED APPLICATIONS

This application is a national stage application (under 35 U.S.C. § 371) of PCT/NZ2019/050055, filed May 22, 2019, which claims benefit of Australian Application No. 2018902200, filed Jun. 20, 2018, which are incorporated herein by reference in their entireties.

FIELD OF THE INVENTION

This invention relates to a magnet for use in a magnetic resonance imaging (MRI) apparatus, and to an apparatus utilising the magnet.

BACKGROUND

MRI apparatuses for medical applications are typically large and cumbersome devices, sized to receive a substantial part of a patient's body, or even the patient's entire body. Whilst this enables the MRI apparatus to be used for analysis of all parts of the patient's body, a large amount of space and significant financial investment are required for the apparatus.

Many patients feel claustrophobic when they are inside a typical MRI apparatus, because a substantial part of their body is received in the apparatus for an extended period during MRI imaging. This is exacerbated by the apparatus typically having a narrowly dimensioned patient recess. MRI magnet cost and complexity scales with recess diameter; patient comfort is therefore traded against having a cost-effective and relatively simple apparatus. Imaging of the brain can be particularly uncomfortable, since the head must be positioned at the centre of the patient recess, leading to feelings of claustrophobia. A related limitation is that the compact size of the patient recess makes interaction between a medical provider and the patient difficult, with sound (via headphones) and limited hand gestures of the patient typically being the only means of communication and interaction with the patient.

MRI apparatuses that are sized for imaging a specific portion of a patient's body are also known. For example, MRI apparatuses have been designed to receive a patient's head and a major portion of their torso. These devices share many of the disadvantages of the typical MRI apparatuses described above. In order to achieve the required field uniformity, large magnets are required, leading to bulky devices that are difficult to transport. Patients may still experience claustrophobia because their head is received by a narrowly dimensioned recess which they cannot see out of. Interaction between a medical provider and the patient is still difficult. Because the patient's shoulders and a major portion of their torso are received by the apparatus, the ability to communicate with a medical provider via hand gestures is not significantly improved.

A typical MRI magnet utilises coils of superconducting material to provide a sufficiently uniform magnetic field to obtain suitable images. When MRI magnets are configured to receive a substantial part of the patient's body, a large magnet or magnets are required. Low temperature superconducting (LTS) material is often used in the coils of the magnets as it is relatively cost-effective and a large amount of the material is required to form the large magnet(s). However, LTS material typically requires the use of a liquid helium cryogen bath to obtain the required operating temperature. Such a cryogen bath is difficult to manufacture, difficult to seal, and adds to the bulk and cost of the apparatus. LTS superconductors also require isothermal radiation shielding to minimise the leakage of thermal radiation to superconducting coils. Again, the shielding adds to the cost, complexity, and bulk of the apparatus.

Conventional MRI apparatuses are typically considered to require very high magnetic field uniformity of less than about 10 ppm peak-to-peak field variation over the imaging volume, and often less than about 2 ppm peak-to-peak field variation, to obtain satisfactory MRI images. Conventional design practice necessitates the use of a large amount of conductor material to achieve these design targets if a relatively compact magnet is required.

The amount of conductor material required to achieve a given field uniformity over the imaging volume is proportional to the longitudinal length of the magnet bore. For a given inner diameter of a magnet (the 'warm bore' diameter), the amount of conductor material required to achieve a given field uniformity increases generally exponentially as the magnet length decreases. For example, it is known that for 1.5 T axisymmetric magnets to achieve a 10 ppm peak-to-peak imaging volume having a transverse dimension that is about half the warm bore diameter, the minimum ratio of magnet length to bore diameter is approximately 1.2. A 1.5 T magnet with a ratio of magnet length to bore diameter of less than 1.2 would generally require a very large amount of conductor material required, making it impractical to construct.

The warm bore must be large enough to receive a gradient coil and at least one radio frequency (RF) coil, such that the resulting inner diameter of the MRI apparatus has enough space to receive at least a portion of a patient's body. It will be appreciated that there are physical constraints on reducing the diameter of the warm bore in order to reduce the conductor material requirement and produce a compact magnet.

It is an object of at least preferred embodiments of the present invention to provide a magnet for use in an MRI apparatus and/or an MRI apparatus that addresses at least one of the disadvantages outlined above, or that at least provides the public with a useful alternative.

SUMMARY OF THE INVENTION

In accordance with a first aspect of the present invention, there is provided a magnet for use in an apparatus for performing magnetic resonance imaging (MRI) of a patient's head, wherein the magnet is an asymmetric magnet comprising a plurality of superconducting coils that are positioned around a cylindrical axis to provide a magnetic field on the cylindrical axis, the cylindrical axis defining an axial direction of the magnet, wherein the magnet comprises: a patient end arranged to be positioned adjacent or against a patient's shoulders with the patient's shoulders outside the magnet; and a recess for receipt of the patient's head extending into the magnet from the patient end, wherein the magnet is configured to provide an offset imaging volume in the recess, wherein the imaging volume has an isocentre that is positioned closer to the patient end of the magnet than to the opposite end of the magnet; wherein the magnet comprises at least three groups of coils in a generally tapering arrangement, with a first group of coils positioned at or toward the patient end having a larger transverse outer dimension than a transverse outer dimension of a second group of coils positioned further from the patient end, and a third group of coils positioned at or toward an opposite end of the magnet having a transverse outer dimension that is smaller than the transverse outer dimension of the second group of coils; and wherein the magnet further comprises an additional group of coils, wherein the first group of coils overlaps the additional group of coils in the axial direction, such that a bottom portion of the additional group of coils is positioned closer to the patient end of the magnet than a top portion of the first group of coils.

As used herein, the term 'asymmetric magnet' means that the magnet is not axisymmetric about a plane that is orthogonal to the cylindrical axis and that is centred at the isocentre of the imaging volume.

In an embodiment, the magnet further comprises a fourth group of coils in a generally tapering arrangement with the first, second, and third groups of coils.

In an embodiment, the fourth group of coils is positioned between the second group of coils and the third group of coils.

In an embodiment, the fourth group of coils has a transverse outer dimension that is smaller than the transverse outer dimension of the second group of coils, and larger than the transverse outer dimension of the third group of coils.

In an embodiment, the first, second, and third groups of coils are arranged to provide a summation of magnetic field from the first, second, and third groups of coils and provide a magnetic field in a first sense. In an embodiment, the first, second, third, and fourth groups of coils are arranged to provide a summation of magnetic field from the first, second, third and fourth groups of coils and provide a magnetic field in a first sense.

In an embodiment, the groups of coils arranged to provide a magnetic field in the first sense have the same winding direction, e.g. a positive or clockwise winding direction.

In an embodiment, the additional group of coils is arranged to provide a magnetic field in a second sense that is opposite to the first sense.

In an embodiment, the additional group of coils has a winding direction opposite to the groups of coils arranged to provide a magnetic field in the first sense, e.g. a negative or anti-clockwise winding direction.

In an alternative embodiment, all coils are wound in the same direction but the additional group of coils is operatively connected to receive current in an opposite sense to the current that is received by the groups of coils arranged to provide a magnetic field in the first sense.

In an embodiment, the top portion of the first group of coils is positioned closer to the patient end of the magnet than a top portion of the additional group of coils.

In an alternative embodiment, the top portion of the first group of coils is not positioned closer to the patient end of the magnet than a top portion of the additional group of coils.

In an embodiment, at least the bottom portion of the additional group of coils has a transverse outer dimension that is smaller than a transverse inner dimension of at least the top portion of the first group of coils.

In an embodiment, the additional group of coils has a transverse outer dimension that is smaller than a transverse inner dimension of the first group of coils.

In an embodiment, the magnet is configured to only receive the patient's head and optionally part of the patient's neck, such that the magnet is configured for use as part of a head-only MRI apparatus. In an embodiment, the magnet is configured to provide an imaging volume that is sized and positioned to overlay a typical adult patient's brain.

In an embodiment, the magnet defines the cylindrical axis, and the recess and the imaging volume are coaxial with the cylindrical axis.

In an embodiment, the isocentre is positioned less than about 180 mm from the patient end of the magnet. In an embodiment, the isocentre is positioned more than about 130 mm from the patient end, optionally more than about 140 mm from the patient end, optionally more than about 150 mm from the patient end, optionally more than about 160 mm from the patient end, optionally more than about 170 mm from the patient end. In an embodiment, the isocentre is positioned about 175 mm from the patient end.

In an embodiment, the isocentre is positioned less than about 175 mm above a patient end of the first group of coils, optionally less than about 165 mm above the patient end of the first group of coils, optionally at about 160 mm above the patient end of the first group of coils, optionally less than about 160 mm above the patient end of the first group of coils. In an embodiment, the isocentre is positioned more than about 75 mm above the patient end of the first group of coils.

In an embodiment, the isocentre is positioned less than about 240 mm below a top of the third group of coils, optionally less than about 230 mm below the top of the third group of coils, optionally less than about 225 mm below the top of the third group of coils, optionally at about 223 mm below the top of the third group of coils. In an embodiment, the isocentre is positioned more than about 195 mm below the top of the third group of coils.

In an embodiment, the magnet has a length from the patient end to the opposite end of less than about 450 mm, optionally less than about 440 mm, optionally less than about 430 mm, optionally less than about 425 mm, optionally about 420 mm. In an embodiment, the magnet has a length from the patient end to the opposite end of 422 mm. In an embodiment, the magnet has a length from the patient end to the opposite end of more than about 350 mm.

In an embodiment, at least some of the groups of coils comprise double pancake coils. In an embodiment, substantially all of the groups of coils comprise double pancake coils.

Additionally or alternatively, at least some of the groups of coils may comprise layer-wound coils.

In an embodiment, the superconducting coils comprise low temperature superconducting (LTS) material. In an embodiment, the coils comprise Niobium-Tin ($Nb_3Sn$) material or Niobium-Titanium (NbTi) material.

In an embodiment, the coils comprise a superconductive material with a critical temperature that is greater than 20 K. In an embodiment, the coils comprise Magnesium Diboride ($MgB_2$) material.

In an embodiment, the coils comprise high temperature superconducting (HTS) material. In an embodiment, the coils comprise rare-earth barium copper oxide (REBCO) material. In an embodiment, the coils comprise Bismuth-Strontium-Calcium-Copper-Oxide (BSCCO) material.

In an embodiment, at least one of the groups of coils consists of one coil. In an embodiment, all of the groups of coils each consist of one coil. In an embodiment, the coil comprises LTS material.

In an embodiment, at least one of the groups of coils consists of a plurality of coils. In an embodiment, all of the groups of coils each consist of a plurality of coils. In an embodiment, the plurality of coils comprises HTS material.

In an embodiment, no isothermal radiation shield is provided between the coils and room temperature surfaces of the magnet. In an embodiment, an isothermal radiation shield is provided between the coils and the room temperature surfaces of the magnet.

In an embodiment, the coils are annular coils that surround the recess. In an embodiment, the coils are coaxial with the cylindrical axis.

In an embodiment, the imaging volume has a substantially ellipsoidal shape.

In an embodiment, the imaging volume comprises magnetic field variation of more than about 50 ppm peak-to-peak and up to about 1000 ppm peak-to-peak over the imaging volume. In an embodiment, the imaging volume comprises magnetic field variation of more than about 100 ppm peak-to-peak and up to about 1000 ppm peak-to-peak over the imaging volume. In an embodiment, the imaging volume comprises magnetic field variation of more than about 200 ppm peak-to-peak and up to about 1000 ppm peak-to-peak over the imaging volume. In an embodiment, the imaging volume comprises magnetic field variation of more than about 250 ppm peak-to-peak and up to about 1000 ppm peak-to-peak over the imaging volume. In an embodiment, the imaging volume comprises magnetic field variation of more than about 300 ppm peak-to-peak and up to about 1000 ppm peak-to-peak over the imaging volume.

In an embodiment, the imaging volume comprises magnetic field variation of more than about 50 ppm peak-to-peak and up to about 800 ppm peak-to-peak over the imaging volume. In an embodiment, the imaging volume comprises magnetic field variation of more than about 50 ppm peak-to-peak and up to about 600 ppm peak-to-peak over the imaging volume. In an embodiment, the imaging volume comprises magnetic field variation of more than about 50 ppm peak-to-peak and up to about 500 ppm peak-to-peak over the imaging volume. In an embodiment, the imaging volume comprises magnetic field variation of more than about 50 ppm peak-to-peak and up to about 400 ppm peak-to-peak over the imaging volume. In an embodiment, the imaging volume comprises magnetic field variation of more than about 50 ppm peak-to-peak and up to about 350 ppm peak-to-peak over the imaging volume. In an embodiment, the imaging volume comprises magnetic field variation of about 313 ppm peak-to-peak over the imaging volume.

In an embodiment, the imaging volume has a length of about 150 mm and a transverse dimension of about 200 mm.

In an embodiment, the magnet comprises a window to enable a patient to see out of the magnet when their head is positioned in the recess. In an embodiment, the window comprises an opening that extends through a wall of the magnet from the recess to an exterior of the magnet. In an embodiment, the window is positioned between the second group of coils and the additional group of coils. In an embodiment, the window comprises a transparent material that covers at least part of the opening.

In accordance with a second aspect of the present invention, there is provided an MRI apparatus for imaging a patient's head, the MRI apparatus comprising the magnet outlined above in relation to the first aspect.

In an embodiment, the MRI apparatus is a head-only MRI apparatus.

The term 'comprising' as used in this specification and claims means 'consisting at least in part of'. When interpreting statements in this specification and claims which include the term 'comprising', other features besides the features prefaced by this term in each statement can also be present. Related terms such as 'comprise' and 'comprised' are to be interpreted in a similar manner.

Any of the above aspects of the invention may include any one or more of the features and/or functionality outlined above or herein in relation to any of the other aspects of the invention. Additionally, any of the above aspects may be provided in suitable combination(s), such as those outlined in relation to other aspects, to provide desired functionality.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

This invention may also be said broadly to consist in the parts, elements and features referred to or indicated in the specification of the application, individually or collectively, and any or all combinations of any two or more said parts, elements or features.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

As used herein the term '(s)' following a noun means the plural and/or singular form of that noun.

As used herein the term 'and/or' means 'and' or 'or', or where the context allows both. The invention consists in the foregoing and also envisages constructions of which the following gives examples only.

BRIEF DESCRIPTION OF THE DRAWINGS

The present invention will now be described by way of example only and with reference to the accompanying drawings in which:

FIG. 6(a) is a front view of the magnet, FIG. 6(b) is a top view of the magnet, FIG. 6(c) is a sectioned side view of the magnet, FIG. 6(d) is a sectioned side view showing a patient's head in position in the recess of the magnet, and FIG. 6(e) is a sectioned front view showing a patient's head in position in the recess of the magnet;

DETAILED DESCRIPTION OF PREFERRED EMBODIMENTS

General Description

Figure 1:
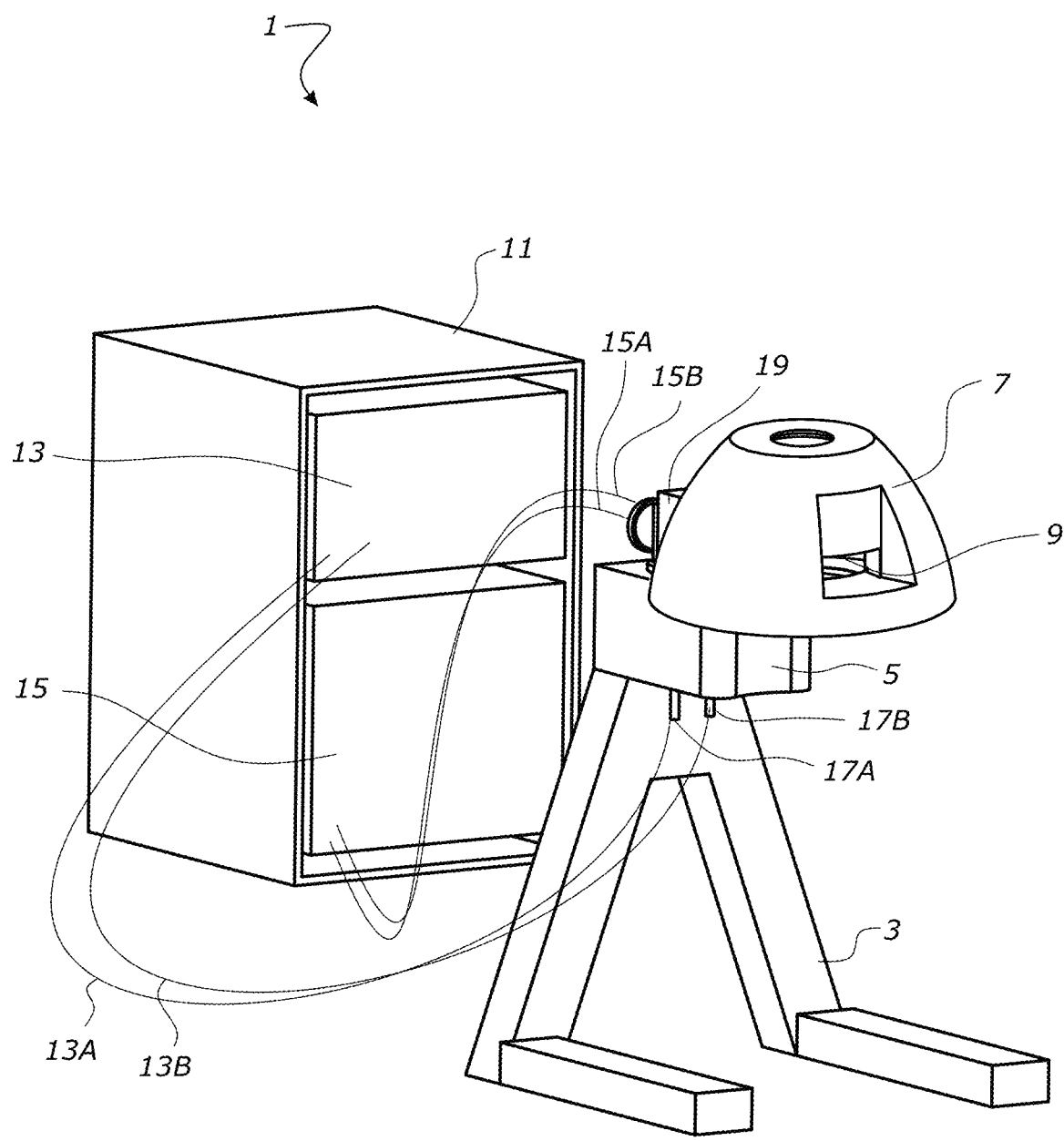
FIG. 1 is a perspective view of a head-only magnetic resonance imaging apparatus in accordance with an embodiment of the present invention.

FIG. 1 shows a schematic drawing of a head-only MRI apparatus 1 for performing magnetic resonance imaging (MRI) of a patient's head. The apparatus 1 comprises a stand 3, a manifold box 5 located at or adjacent the top of the stand 3 and supported by the stand 3, and a magnet 7 connected to the manifold box 5. The magnet has a window 9. An equipment rack 11 is provided which comprises a power supply and controller 13 and a helium compressor 15. The power supply and controller 13 provides current to the magnet 7 via current leads 13A, 13B that are connected to the magnet coils through current injection points 17A, 17B mounted on the manifold box 5. The helium compressor 15 provides compressed helium via helium lines 15A, 15B to the cryocooler 19 which in turn cools the magnet 7.

FIG. 2, FIG. 3, FIG. 4 and FIG. 5 schematically show a perspective view, an exploded perspective view, a front view and a side view respectively of a patient P in position in the apparatus.

Reference herein to a patient is to an averagely sized adult human patient.

Figure 2:
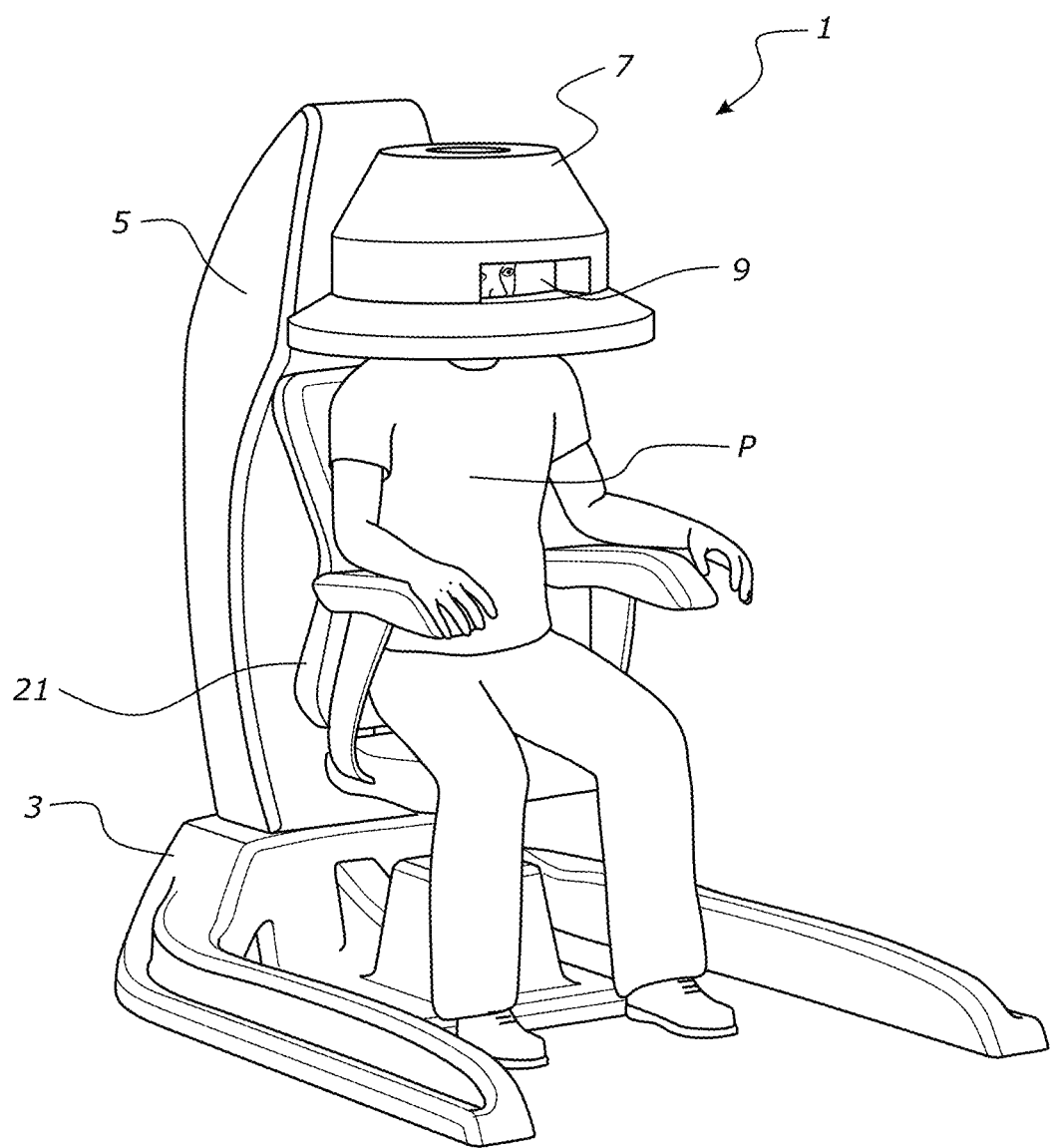
FIG. 2 is a schematic perspective view similar to FIG. 1, but showing a patient in position in the apparatus.

The stand 3 may be configured for use by a patient in a standing position or in a seated position. As shown in FIG. 2, the stand 3 may have a seat 21 for supporting the patient P in a seated configuration. The seat 21 may be height adjustable.

In an alternative embodiment (not shown), the apparatus 1 may be configured for use by a patient that is lying down. The terms 'top' and 'bottom' as used herein define relative locations in relation to a vertically oriented magnet 7. If the magnet 7 is used in an orientation other than vertical, for example a horizontal orientation, the terms 'top' and 'bottom' should be interpreted as referring to respective ends of the magnet, and should not be considered to limit the orientations in which the magnet 7 can be used.

It can be seen from FIG. 2 that in use of the apparatus 1, the patient's head is positioned in the magnet 7 with their eyes aligned with a window 9 of the magnet 7 so the patient can see outside the magnet and respond to visual cues outside the magnet 7.

Figure 3:
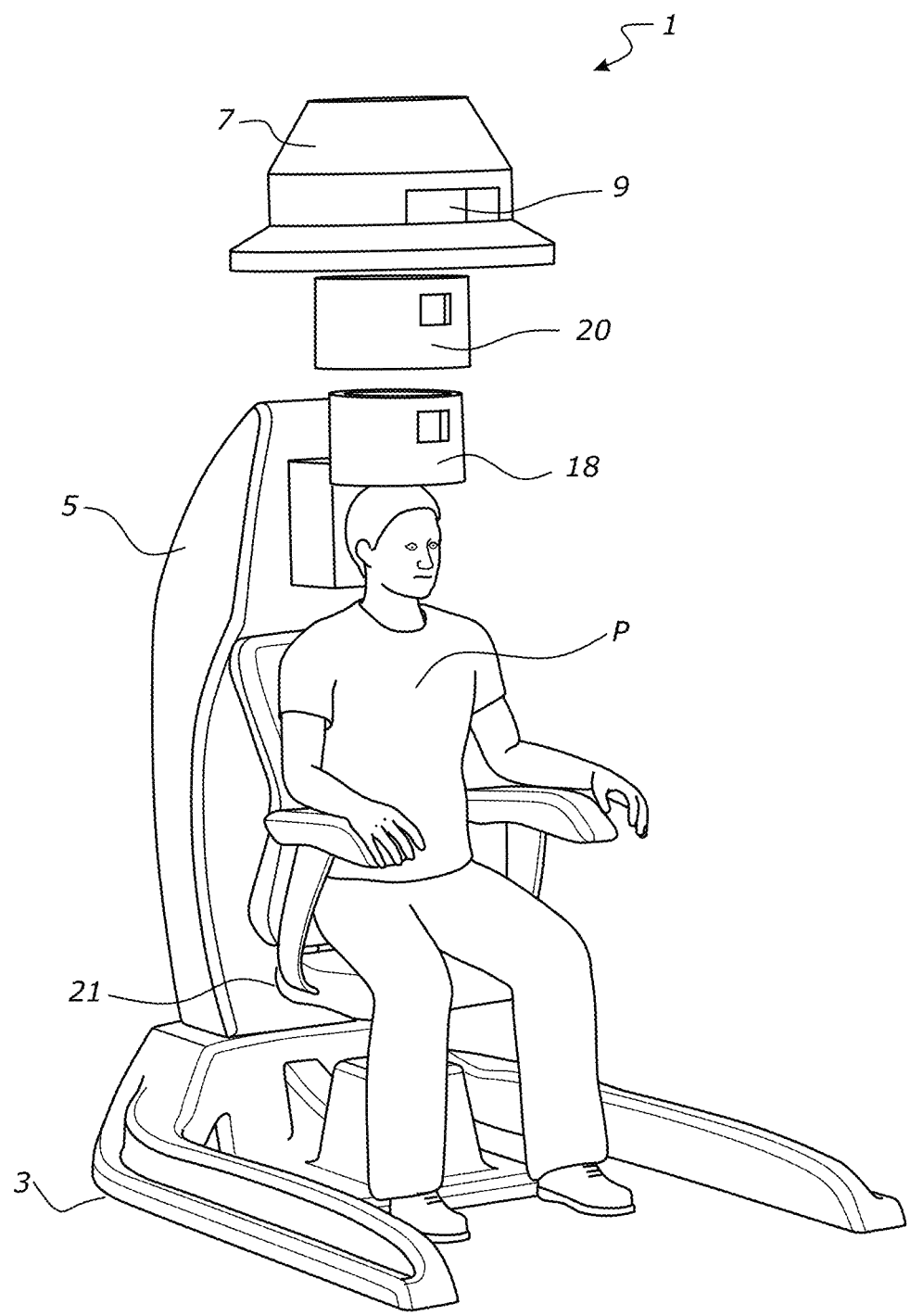
FIG. 3 is a schematic perspective view similar to FIG. 2, but showing an exploded view of the apparatus.
Figure 4:
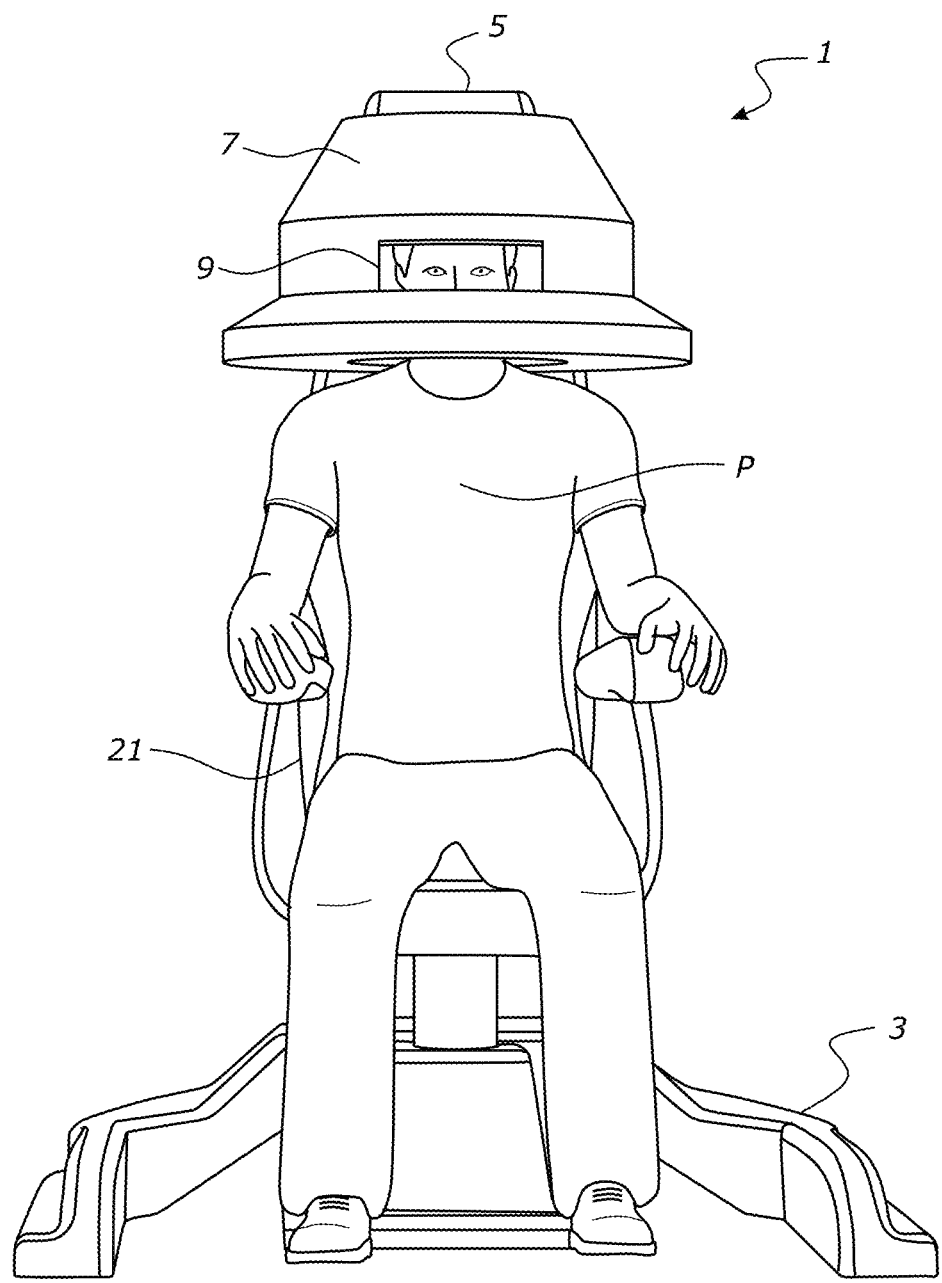
FIG. 4 is a schematic front view similar to FIG. 2.
Figure 5:
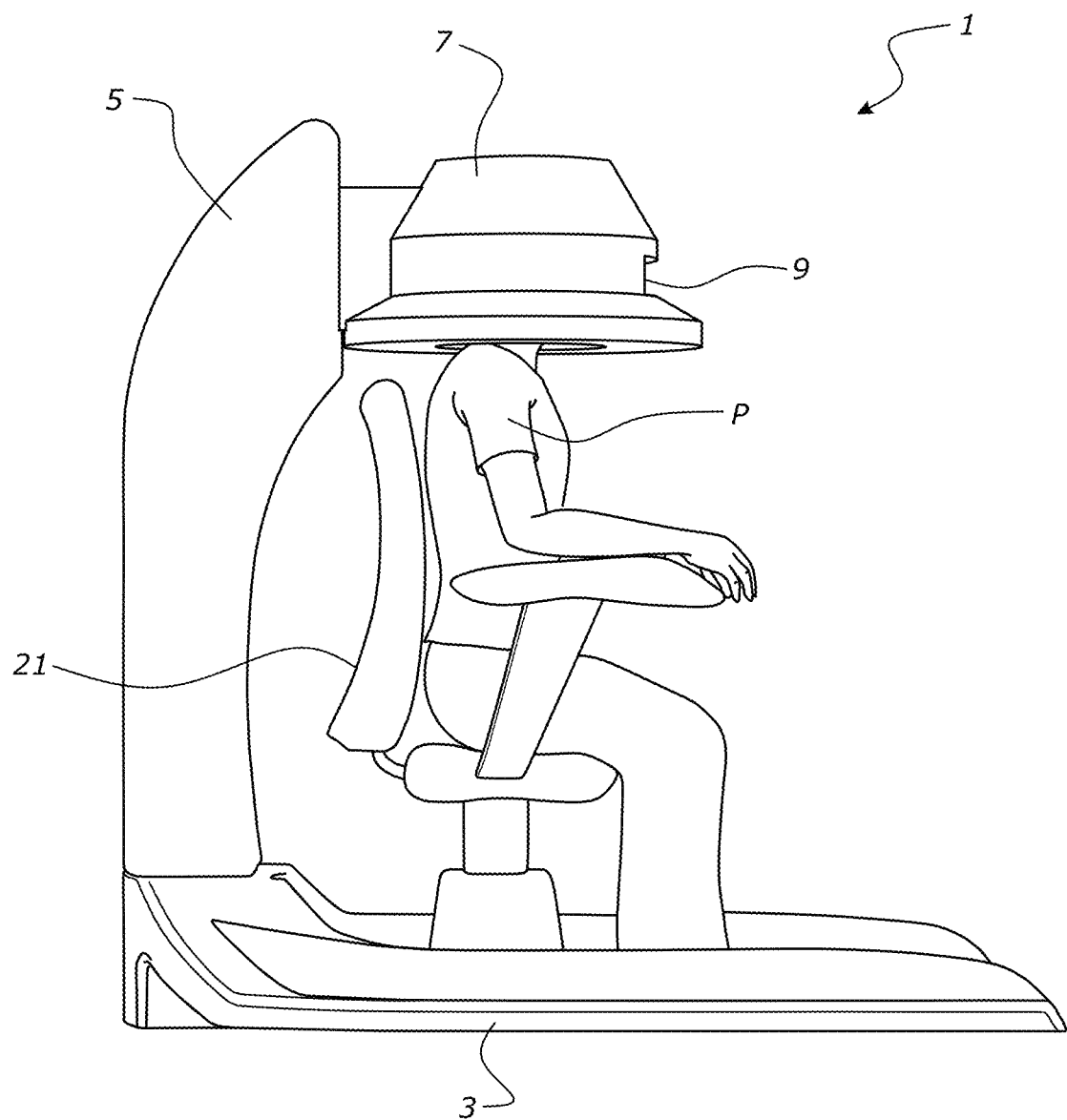
FIG. 5 is a schematic side view similar to FIG. 2.

Referring to FIG. 3, the MRI apparatus 1 also comprises a radio frequency (RF) coil assembly 18, and a gradient coil 20. Not illustrated but provided are suitable RF and gradient amplifiers and a spectrometer to control the MRI apparatus. FIG. 3 shows how the RF coil assembly 18 and the gradient coil 20 may be positioned relative to the magnet. The RF coil assembly 18 is used to transmit RF pulses and hence excite spin magnetization within the imaging volume according to the requirements of the particular MRI pulse sequence. The gradient coil 20 applies pulsed field gradients in at least two planes to encode the region within the imaging volume that is to be imaged. The spectrometer synchronises the gradient and RF pulses and performs the signal acquisition according to the requirements of the particular MRI pulse sequence. The RF and gradient amplifiers amplify the gradient and RF signals from the spectrometer. The RF pre-amplifier(s) amplify the MRI signal before reception into the spectrometer.

The RF coil assembly 18, gradient coil 20, amplifiers and spectrometer are used in the generation of pulse sequences for obtaining MRI images. Suitable pulse sequences are discussed in more detail later in the specification.

Magnet

Figure 6:
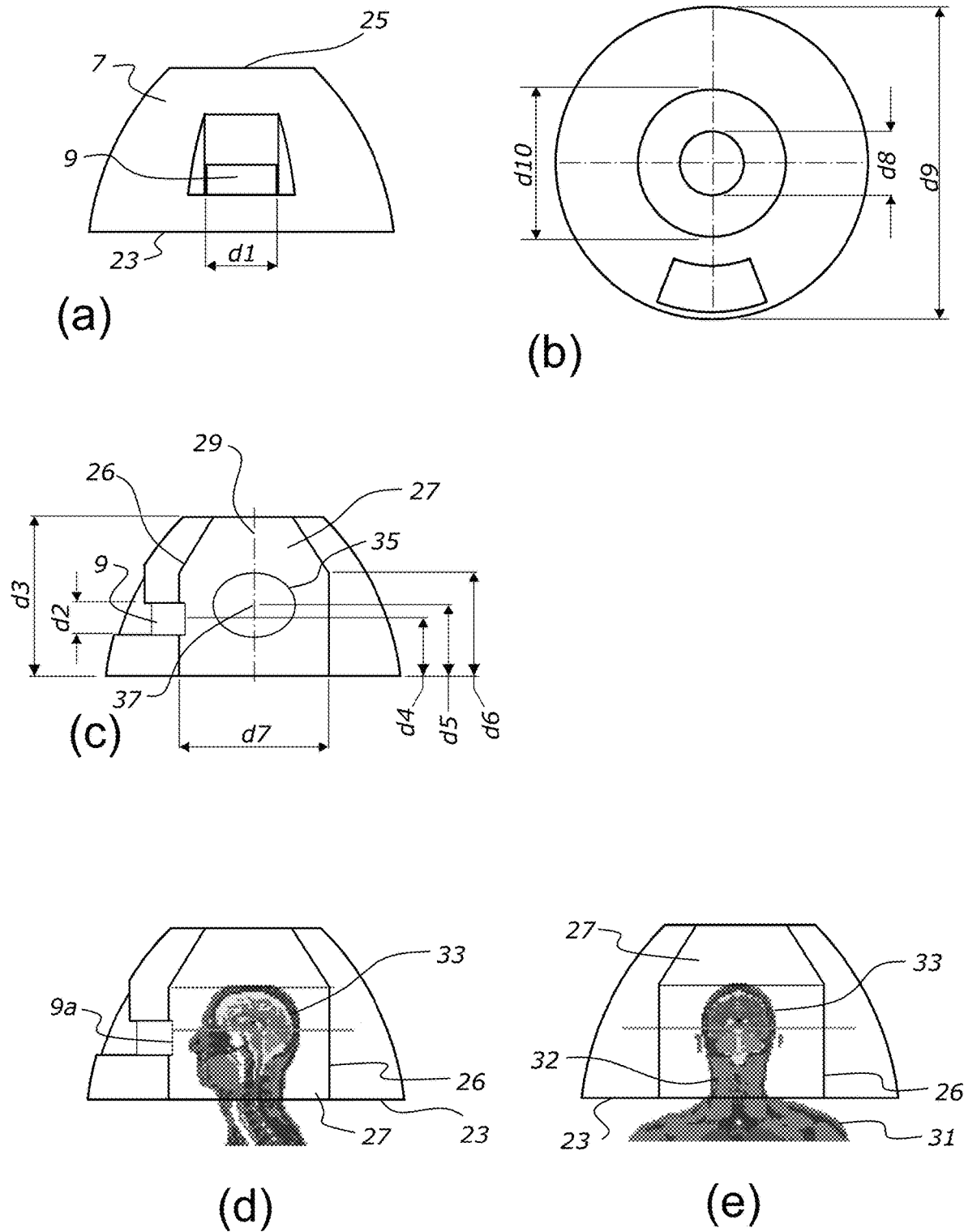
FIG. 6 is a simplified view of the magnet of the apparatus of FIG. 1, where

FIGS. 6(*a*)-(*e*) show a simplified view of an exemplary magnet 7 for use in the apparatus 1. The magnet 7 is an asymmetric magnet, and comprises a plurality of superconducting coils that are positioned around a cylindrical axis 29 and spaced along said axis to provide a magnetic field on the cylindrical axis. The cylindrical axis 29 defines an axial direction of the magnet 7. The magnet 7 comprises a patient end 23 arranged to be positioned adjacent or against a patient's shoulders 31 with the patient's shoulders 31 outside the magnet 7, as shown in FIGS. 2, 4, 5, and 6(*e*). The patient end 23 may be positioned slightly above a patient's shoulders 31 or may contact the top of the patient's shoulders 31. The magnet 7 further comprises a recess 27 for receipt of the patient's head 33 and extending into the magnet 7 from the patient end 23 as shown in FIGS. 6(*d*) and 6(*e*). The magnet recess 27 may have a transverse dimension (e.g. diameter) that is smaller than the width of a patient's shoulders. The magnet recess 27 is defined by a warm bore 26 of the magnet.

The magnet 7 is configured to provide an offset imaging volume 35 in the recess 27 as shown in FIG. 6(*c*). The imaging volume has an isocentre that is closer to the patient end of the magnet than to the opposite end of the magnet. In the embodiment shown in FIG. 6, the imaging volume 35 has an isocentre 37 that is positioned less than about 180 mm from the patient end 23 of the magnet to accommodate the relative height of the head and shoulders of most human adults, to align the isocentre 37 with the centre of the patient's brain. In an embodiment, the isocentre 37 is positioned more than about 130 mm from the patient end 23, or more than about 140 mm from the patient end 23, or more than about 150 mm from the patient end 23, or more than about 160 mm from the patient end 23, or more than about 170 mm from the patient end 23. In an embodiment, the isocentre 37 is positioned about 175 mm from the patient end 23.

The magnet 7 is configured to only receive the patient's head 33 and optionally part of the patient's neck 32, such that the magnet 7 is configured for use as part of a head-only MRI apparatus 1. The magnet 7 is configured to provide an imaging volume 35 that is sized and positioned to overlay a typical adult patient's brain. The imaging volume 35 is a substantially ellipsoidal shape, having a relatively large transverse dimension and a relatively short dimension along the cylindrical axis.

The magnet 7 defines a cylindrical axis 29. The recess 27 and the imaging volume 35 are coaxial with the cylindrical axis 29. The imaging volume 35 is positioned closer to the patient end 23 of the magnet 7 than to an opposite end 25 of the magnet, along the cylindrical axis 29.

In an embodiment, the magnet 7 has a length from the patient end 23 to the opposite end 25 of less than about 450 mm, or of less than about 440 mm, or of less than about 430 mm, or of less than about 425 mm, or of about 420 mm. In the embodiment shown in FIG. 6, the magnet 7 has a length from the patient end 23 to the opposite end 25 of 422 mm. In an embodiment, the magnet 7 has a length from the patient end 23 to the opposite end 25 of more than about 350 mm. In other embodiments, the length may be longer or shorter.

The magnet 7 comprises a window 9 to enable a patient to see out of the magnet 7 when their head 33 is positioned in the recess 27. The window 9 comprises an opening that extends through a wall of the magnet 7 from the recess 27 to an exterior of the magnet 7. In an embodiment, the window 9 comprises an at least partially transparent material 9a that covers at least part of the opening, such as glass or a polymer material. In an embodiment, the magnet is part of a Faraday cage and the window covering 9a comprises a conductive material such as copper mesh, indium tin oxide, a conductive polymer or glass coated in a transparent conductor. In an embodiment, the magnet 7 does not have a window.

Figure 7:
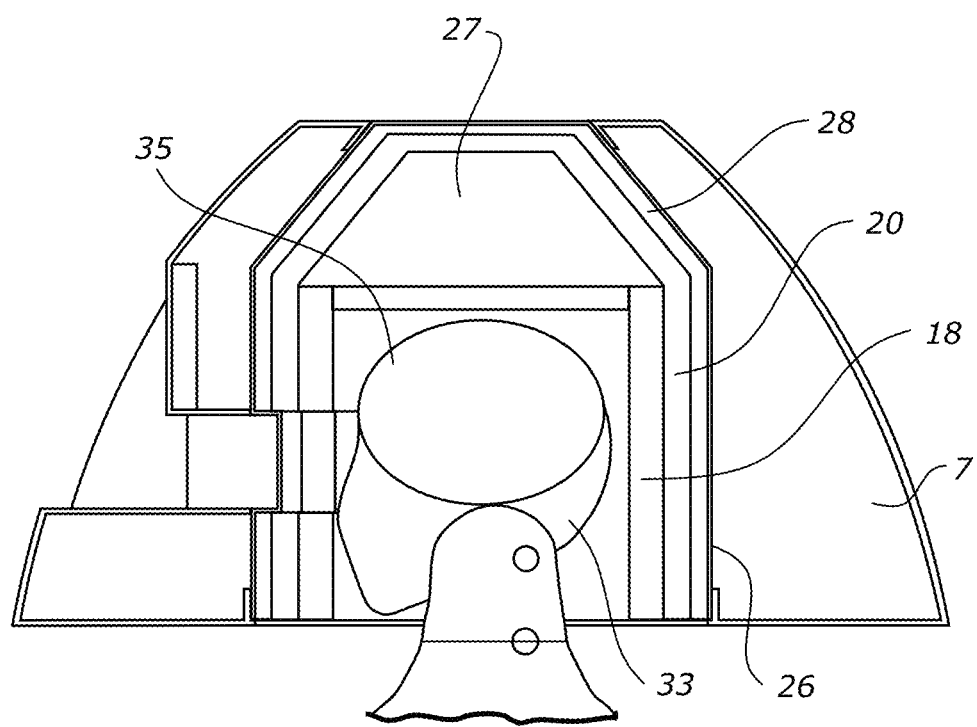
FIG. 7 is a simplified sectional side view of an exemplary head-only MRI apparatus with a patient's head received in the apparatus.

The magnet may comprise passive shims 28 (see FIG. 7). Passive shims 28 are formed from a ferromagnetic material and may be used to correct for the difference in homogeneity between designed and as-built magnetic fields.

Exemplary dimensions for one possible configuration of the magnet 7 are provided below. It will be appreciated that other configurations are within the scope of the invention.

Window 9: d1=180 mm in the transverse direction, d2=77 mm in the vertical direction.

Total height of magnet 7: d3=422 mm in the vertical direction.

Height of centre of window 9: d4=135 mm from the patient end 23 of the magnet 7.

Height of isocentre 37 of imaging volume 35: d5=175 mm from the patient end 23 of the magnet 7.

Height of cylindrical portion 75: d6=294 mm from the patient end 23 of the magnet 7.

Inner diameter of the bottom of the warm bore 26: d7=375 mm.

Inner diameter of the top of the warm bore 26: d8=161 mm.

Outer diameter of the bottom part of the magnet 7: d9=784 mm.

Outer diameter of the top part of the magnet: d10=370 mm.

FIG. 7 shows a sectional view of an exemplary head-only MRI apparatus 1 having a magnet 7 (coils not illustrated) with a warm bore 26, passive shims 28, a gradient coil 20, and an RF coil assembly 18. The inner diameter of the non-tapered section of the magnet warm bore 26 is about 375 mm. The passive shims 28, gradient coil 20 and RF coil assembly 18 may have any suitable dimensions. For example, the inner diameter of the non-tapered section of the passive shims 28 may be about 345 mm. The inner diameter of the non-tapered section of the gradient coil 20 may be about 300 mm. The inner diameter of the RF coil assembly 18 may be about 245 mm. The diameter of the RF coil assembly 18 is large enough to receive an adult human head 33. The imaging volume 35 overlays the patient's brain. The exemplary magnet 7 will now be discussed in more detail with reference to FIGS. 8 to 10.

Figure 8:
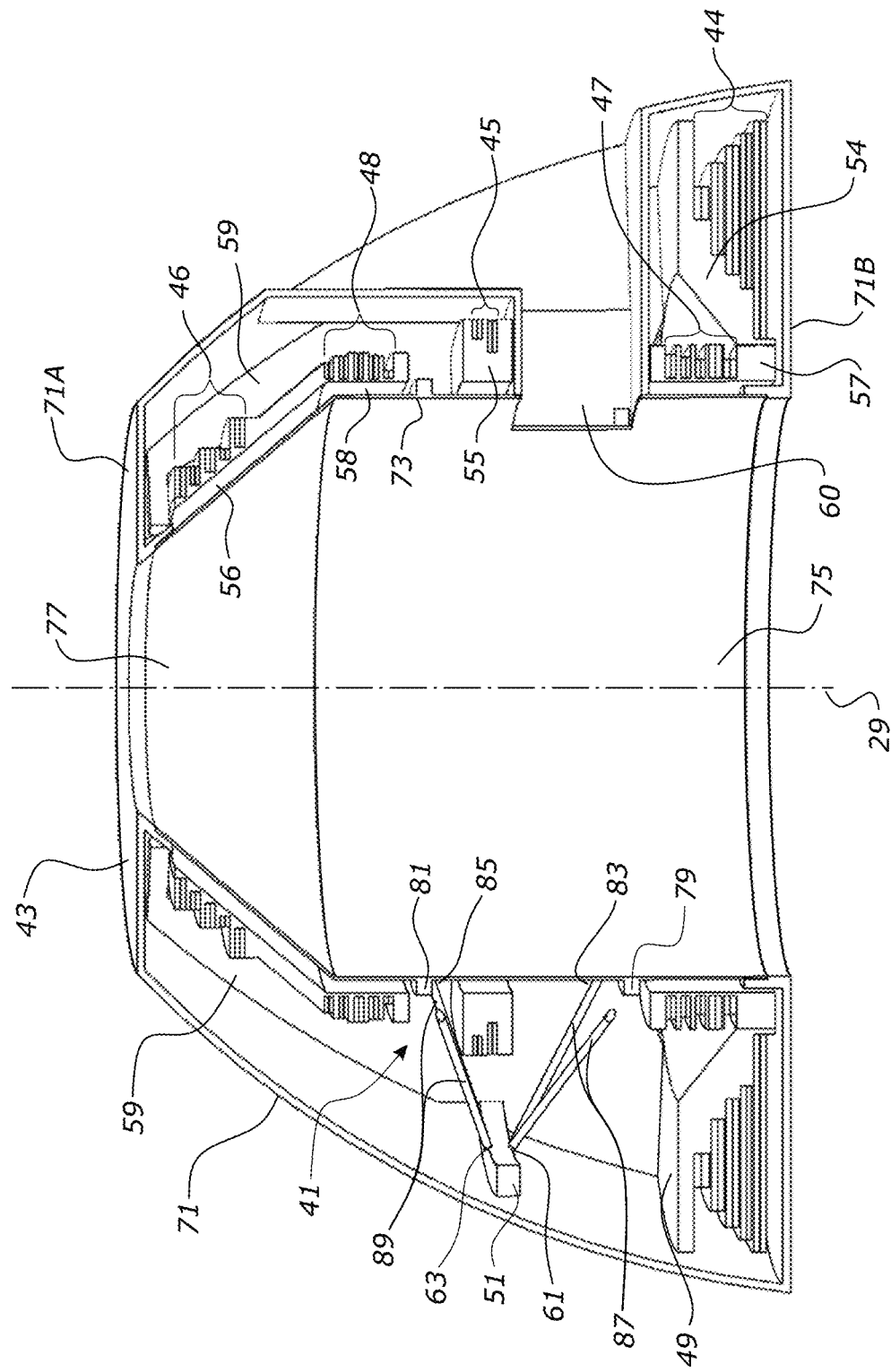
FIG. 8 is a sectional perspective view of an exemplary magnet.

FIG. 8 shows a detailed cross-sectional view of the exemplary magnet 7. The magnet 7 comprises a coil pack 41 suspended within a cryostat 43. In an embodiment, no isothermal radiation shield is provided between the coil pack 41 and the room temperature surfaces of the magnet 7, so that the lowest coils can be positioned close to the patient end 23 of the magnet 7 to provide a compact magnet. That is, the coil pack 41 is isothermally unshielded from the room temperature surfaces of the magnet 7.

Coil Pack

The coil pack 41 comprises five groups of coils 44, 45, 46, 47, 48 mounted on a coil former 49. The coil former 49 prevents coil movement or deflection under normal operating circumstances. The coil former 49 may be made from a substantially non-ferromagnetic material such as stainless steel or aluminium.

The coil pack 41 is wrapped in a low emissivity material (not shown) to limit the radiation heat load onto the coil pack 41 in place of an isothermal radiation shield. In an embodiment an isothermal radiation shield is used in addition to the low emissivity material. In an embodiment, the low emissivity material is multi-layer insulation, such as RUAG Coolcat.

Coil Former

An example of a coil former 49 comprises coil-retaining portions 54, 55, 56, 57, 58 adapted to retain the groups of coils 44, 45, 46, 47, 48 in the magnet 7. The coil-retaining portions 54, 55, 56, 57, 58 may comprise annular flanges for retaining the coils in each group of coils 44, 45, 46, 47, 48. The coil-retaining portions 54, 55, 56, 57, 58 may be integrally formed, and/or connected by other means. In the embodiment shown, the coil-retaining portions 56, 58 that retain the third and fourth groups of coils 46, 48 are integrally formed. The coil-retaining portions 54, 55, 56, 57, 58 are also connected via a plurality of radially spaced ribs 59. An annular ring 51 extends around an outer portion of the ribs 59.

One or more shims (not illustrated) made from an insulating material may be used to correctly position the coils on the coil former.

The ribs 59 are arranged so that the window 9 of the magnet 7 is aligned with a space between two ribs 59. Any suitable number of ribs 59 may be used, for example, six, seven, eight, nine, ten, eleven, or twelve ribs.

The annular ring 51 comprises a series of apertures or couplings that may be used for supporting/suspending the coils as discussed in more detail below. In the embodiment shown in FIG. 8, the annular ring 51 comprises two series of apertures or couplings 61, 63. In an embodiment, the apertures or couplings are spaced between the ribs 59. It will be appreciated that any suitable number of apertures or couplings may be used.

A skilled person will appreciate that the coil former could have a different shape and/or configuration, and the coils could be formed/supported in a different way.

Coils

Figure 9:
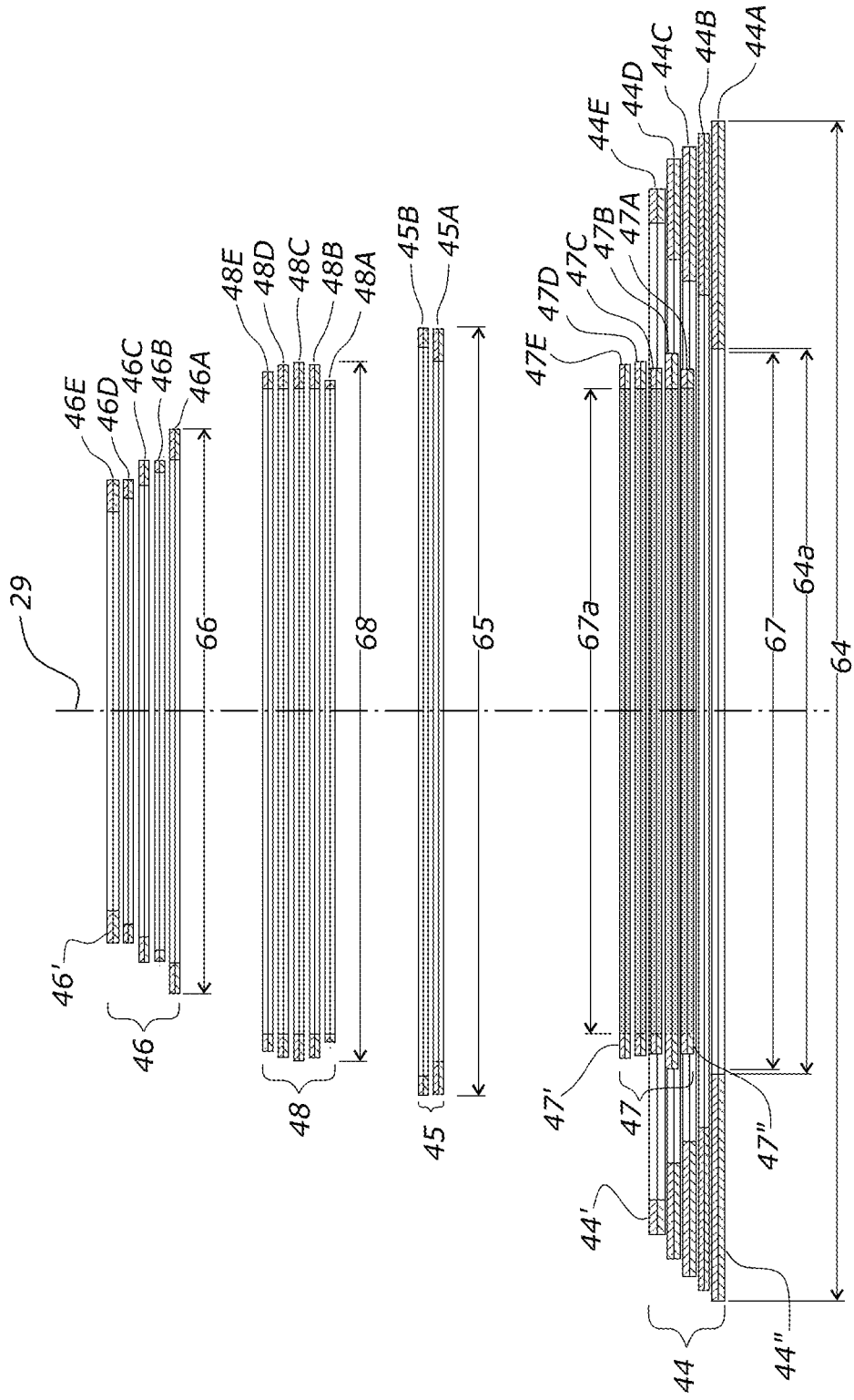
FIG. 9 is a sectional side view of an exemplary arrangement of coils of the magnet.

FIG. 9 shows a sectional side view of an exemplary arrangement of the superconducting coils 44A-E, 45A-E, 46A-E, 47A-E, 48A-E of the magnet 7. The coils 44A-E, 45A-B, 46A-E, 47A-E, 48A-E are annular coils that surround the recess 27. The coils are coaxial with the cylindrical axis 29.

The magnet 7 comprises at least three groups of coils. The coils have a generally tapering arrangement. In the embodiment shown in FIG. 9, the magnet 7 comprises a first group of coils 44 positioned at or toward the patient end 23 that has a first relatively large transverse outer dimension 65, a second group of coils 45 positioned further from the patient end 23 that has a second relatively small transverse outer dimension 66, and a third group of coils 46 positioned at or toward the opposite end that has a third transverse outer dimension 67 that is smaller than the second transverse outer dimension 66. The third group of coils 46 is positioned closer to the opposite end than the second group of coils 45.

The magnet 7 further comprises an additional group of coils 47. The first group of coils 44 overlaps the additional group of coils 47 in the axial direction, such that a bottom portion 47" of the additional group of coils 47 is positioned closer to the patient end 23 of the magnet 7 than a top portion 44' of the first group of coils 44. In an embodiment, the additional group of coils 47 is positioned at least partially inside or within the first group of coils 44.

The additional group of coils 47 is positioned below the second group of coils 45. The additional group of coils 47 is positioned closer to the patient end 23 of the magnet 7 than the second group of coils 45. The window 9 is positioned between the second group of coils 45 and the additional group of coils 47. The additional group of coils 47 in overlapping arrangement with the first group of coils 44 provides a larger gap between the additional group of coils 47 and the second group of coils 45 than if the additional group of coils 47 was positioned above the first group of coils 44. The gap between the additional group of coils 47 and the second group of coils 45 advantageously enables the window 9 to have a suitable viewing angle when a patient's head 33 is positioned within the imaging volume 35. For example, the window 9 may provide a viewing angle of 11°-15°, depending on the size of the patient's head 33.

In the embodiment shown, the magnet 7 further comprises a fourth group of coils 48. The fourth group of coils is arranged in a generally tapering arrangement with the first, second, and third groups of coils. The fourth group of coils is positioned between the second group of coils 45 and the third group of coils 46. The fourth group of coils 48 has a transverse outer dimension that is smaller than the transverse dimension of the second group of coils 45, and larger than the transverse dimension of the third group of coils 46.

In an embodiment, the first 44, second 45, and third 46 groups of coils are arranged to provide a summation of magnetic field from the first 44, second 45, and third 46 groups of coils and provide a magnetic field in a first sense. For example, the first 44, second 45, and third 46 groups of coils have the same winding direction, e.g. a positive or clockwise winding direction, to provide a summation of magnetic field from the first 44, second 45, and third 46, groups of coils.

In the embodiment shown, the first 44, second 45, third 46, and fourth 48 groups of coils are arranged to provide a summation of magnetic field from the first 44, second 45, third 46, and fourth 48 groups of coils and provide a magnetic field in a first sense. For example, the first 44, second 45, third 46 and fourth 48 groups of coils have the same winding direction, e.g. a positive or clockwise winding direction, to provide a summation of magnetic field from the first 44, second 45, third 46, and fourth 48 groups of coils.

The additional group of coils 47 is arranged to provide a magnetic field in a second sense that is opposite to the first sense. For example, the additional group of coils 47 may have a winding direction opposite to the groups of coils arranged to provide a magnetic field in the first sense (the first 44, second 45, third 46, and fourth 48 groups of coils), e.g. a negative or anti-clockwise winding direction. As another example, all coils may be wound in the same direction but the additional group of coils 47 may be operatively connected to receive current in an opposite sense to the current that is received by the groups of coils arranged to provide a magnetic field in the first sense (the first 44, second 45, third 46, and fourth groups of coils).

In an embodiment, the magnet 7 comprises more than one group of coils that is arranged to provide a magnetic field in a second sense that is opposite to the first sense.

In the embodiment shown, the top portion 44' of the first group of coils 44 is positioned closer to the patient end 23 of the magnet 7 than a top portion 47' of the additional group of coils 47. In an alternative embodiment, the top portion 44' of the first group of coils 44 is not positioned closer to the patient end 23 of the magnet 7 than a top portion 47' of the additional group of coils 47; i.e. the top portion 44' of the first group of coils may be positioned further from the patient end 23 than the top portion 47' of the additional group of coils.

In the embodiment shown, the bottom portion 47" of the additional group of coils 47 is positioned inside the opening defined by the transverse inner dimension, or inner diameter, of the top portion of the first group of coils 44. At least the bottom portion 47" of the additional group of coils 47 has a transverse outer dimension 67 that is smaller than a transverse inner dimension 64*a* of at least the top portion of the first group of coils 44. In an embodiment, the additional group of coils 47 has a transverse outer dimension 68 that is smaller than the transverse inner dimension 64*a* of the first group of coils 44.

Exemplary coil dimensions are provided in table 1.

TABLE 1 exemplary coil dimensions

| Coil number | Inner radius (mm) | Outer radius (mm) | Axial position (to centre of coil) from isocentre (mm) | Coil thickness (mm) |
| --- | --- | --- | --- | --- |
| 44A | 225.18 | 366.00 | −155.20 | 8.60 |
| 44B | 258.38 | 358.00 | −146.30 | 7.20 |
| 47A | 200.00 | 212.04 | −136.00 | 8.60 |
| 44C | 266.98 | 350.00 | −137.40 | 8.60 |
| 47B | 200.00 | 221.32 | −126.40 | 8.60 |
| 44D | 279.89 | 339.21 | −127.80 | 8.60 |
| 47C | 200.00 | 212.23 | −116.80 | 6.60 |
| 44E | 302.46 | 324.00 | −117.40 | 10.20 |
| 47D | 200.00 | 213.52 | −107.20 | 6.60 |
| 47E | 200.00 | 215.07 | −97.60 | 7.20 |
| 45A | 217.17 | 237.16 | 17.80 | 6.60 |
| 45B | 225.50 | 238.00 | 27.40 | 6.60 |
| 48A | 200.00 | 204.80 | 85.00 | 6.60 |
| 48B | 200.00 | 214.81 | 94.60 | 6.60 |
| 48C | 200.00 | 216.61 | 104.20 | 6.60 |
| 48D | 200.00 | 214.38 | 113.80 | 6.60 |
| 48E | 200.00 | 210.45 | 123.40 | 6.60 |
| 46A | 156.00 | 174.90 | 181.00 | 6.60 |
| 46B | 148.00 | 154.70 | 190.60 | 6.60 |
| 46C | 140.00 | 155.47 | 200.20 | 6.60 |
| 46D | 132.00 | 143.61 | 209.80 | 6.60 |
| 46E | 124.00 | 143.48 | 219.40 | 7.20 |

The inner diameters of at least one of the groups of coils, for example the top group of coils, may follow a generally arcuate path. The apparatus may have more groups of coils.

The number and position of the coils are determined so as to minimise the length of conductor in light of the ergonomic and homogeneity constraints of the magnet. The exemplary magnet shows how this may be achieved for the constraints used to define this magnet. It will be apparent to those skilled in the art that alternative configurations are possible depending on the specific constraints of the magnet which is desired. For example, a fewer or greater number of coils may be required. Alternatively, the same coil axial positions could be utilised, whilst changing the inner and outer dimeter of the coils. Finally, the same number of coils could be used whilst adjusting the coil axial positions and the coil inner and outer diameters. For example, at least one of the groups of coils could consist of one coil. For example, all of the groups of coils could each consist of one coil. The coil may comprise LTS material. As another example, at least one of the groups of coils could consist of a plurality of coils. For example, all of the groups of coils could each consist of a plurality of coils. The plurality of coils may comprise HTS material.

The coil arrangement provides the asymmetric positioning of the isocentre 37 along the cylindrical axis.

The isocentre 37 is positioned so that a bottom edge of the imaging volume is not positioned lower than the bottom 44" of the first group of coils.

In an embodiment, the isocentre 37 is positioned less than about 175 mm above a patient end 44" of the first group of coils 44, optionally less than about 165 mm above the patient end of the first group of coils, optionally at about 160 mm above the patient end of the first group of coils, optionally less than about 160 mm above the patient end of the first group of coils. In an embodiment, the isocentre 37 is positioned more than about 75 mm above the patient end 44" of the first group of coils.

In an embodiment, the isocentre 37 is positioned less than about 240 mm below a top 46" of the third group of coils 46, optionally less than about 230 mm below the top of the third group of coils, optionally less than about 225 mm below the top of the third group of coils, optionally at about 223 mm below the top of the third group of coils. In an embodiment, the isocentre 37 is positioned more than about 195 mm below the top 46" of the third group of coils 46.

The inner and outer diameters of the coils 44A-E, 45A-B, 46A-E, 47A-E, 48A-E are generally smaller for the coils that are further away from the patient end 23 of the magnet 7. This reduces magnet size and minimises conductor usage.

In an embodiment, at least some of the coils comprise double pancake coils. In an embodiment, substantially all of the coils comprise double pancake coils. Additionally or alternatively, at least some of the coils may comprise layer-wound coils.

In the embodiment shown in FIGS. 8 and 9, all of the coils 44A-E, 45A-B, 46A-E, 47A-E, 48A-E comprise double pancake coils. Double pancake coils comprise two single pancake coils wound around a common axis. The single pancakes in the double pancake coil may share one or more conductors. The two single pancake coils are separated from each other by a thin layer of insulating material. The double pancake coils are insulated top and bottom. Double pancake coils may be stacked up into a group with annular cooling plates between adjacent double pancake coils to allow extraction of heat to the refrigeration source.

Each of the coils of the double pancake or layer wound coil may have an intermediary layer between turns, such as stainless steel, copper or an insulator. It will be appreciated to those skilled in the art that tuning the electrical conductivity of this layer will change the ramping time and quench characteristics of the coil. For double pancake coils wound from REBCO, stainless steel protects the coils against the risk of quench, while avoiding long magnet settling times associated with using a copper intermediary layer. Alternatively, insulation may be used between turns and the magnet quench protected using alternative methods.

In an embodiment, the superconducting coils comprise low temperature superconducting (LTS) material. In an embodiment, the coils comprise Niobium-Tin ($Nb_3Sn$) material or Niobium-Titanium (NbTi) material.

In an embodiment, the coils comprise a superconductive material with a critical temperature that is greater than 20 K. Such a material requires cooling to a higher temperature than LTS materials to achieve superconducting properties. In an embodiment, the coils comprise Magnesium Diboride ($MgB_2$) material.

In an embodiment, the coils comprise high temperature superconducting (HTS) material. In an embodiment, the coils comprise rare-earth barium copper oxide (REBCO) material or Bismuth-Strontium-Calcium-Copper-Oxide (BSCCO) material.

The coils may be wound from a tape of superconductive material. The tape may be laminated with a conductive material. For example, the coils may be wound from a REBCO tape that is laminated with stainless steel.

In the embodiment shown, the coils 44A-E, 45A-B, 46A-E, 47A-E, 48A-E comprise double pancake coils. Referring to table 1, different coils have different heights. The heights include the two coils, and a top, centre and bottom insulation layer. In an alternative embodiment, each double pancake coil 44A-E, 45A-B, 46A-E, 47A-E, 48A-E may be about the same height, for example about 10 mm high. Each coil in the pancake may be about 4 mm high. The thickness and dimensions may vary.

HTS material requires cooling to a higher temperature than LTS material to achieve superconducting properties. Conventional MRI machines utilise LTS materials that typically require cooling to around 4.2 K. By contrast, use of REBCO HTS material allows the magnet 7 to run at around 30 K to achieve around 1.5 T operation.

Higher temperature operation may provide several advantages. Conventional MRI machines typically require isothermal radiation shielding and cryogen baths to achieve the required cooling for LTS material.

The exemplary materials described above are by way of example only and the coils may be formed from any suitable superconducting material.

In the embodiment shown in the figures, no isothermal radiation shield is provided between the coil pack 41 and room temperature surfaces of the magnet 7. This allows the magnet 7 to be more compact and the isocentre 37 of the imaging volume 35 to be located closer to the patient end of the magnet.

Cryostat

The cryostat 43 is a vessel suitable for supporting a high vacuum. The cryostat 43 has suitable penetrations (not shown) for applying vacuum, injecting current and accommodating the cryocooler 19. The cryostat is made, for example, from stainless steel.

The cryostat 43 comprises a vacuum manifold (not illustrated). The cryocooler 19 (shown in FIG. 1) interfaces with the cryostat 43 via the vacuum manifold. The cryocooler is positioned with a portion outside the vacuum manifold in a relatively warm region and a portion inside the vacuum manifold in the cool region. Conductors such as thermally conductive strips, heat pipe, or other conductors are used to transfer heat away from the coils via the cryocooler.

Referring to FIG. 8, the cryostat 43 has an outer shell 71, an inner shell 73 and a slot 60. The inner shell 73 comprises a generally cylindrical lower portion 75 and a frustoconical upper portion 77. The inner shell 73 defines the magnet warm bore 26. The outer shell 71 is shaped to accommodate the shape of the coil pack 41, and has a curved outer surface that extends between a substantially flat top portion 71A and a substantially flat bottom portion 71B. The top portion 71A and the bottom portion 71B are both generally ring-shaped and each have an inner diameter and an outer diameter. The outer diameter of the bottom portion 71B is larger than the outer diameter of the top portion 71A. The inner diameter of the bottom portion 71B is larger than the inner diameter of the top portion 71A. The inner shell 73 and the outer shell 71 are both sized to accommodate the coil pack 41 such that the coil pack 41 does not contact the cryostat 43.

Annular ledges 79, 81 run around a substantial portion of the face of the inner shell 73 that is internal to the cryostat 43. In an embodiment, the annular ledges 79, 81 are made from the same material as the cryostat 43. The annular ledges 79, 81 may be integrally formed as part of the inner shell 73. Alternatively, the annular ledges 79, 81 may be a separate part that is welded to the inner shell 73.

In an alternative embodiment, multiple shorter ledges or lugs are used instead of a single continuous ledge. The shorter ledges or lugs may be integrally formed as part of the inner shell 73. Alternatively, the shorter ledges or lugs may be a separate part that is welded to the inner shell 73.

The annular ledges 79, 81 comprise a series of apertures or couplings 83, 85. In an embodiment, the number of apertures or couplings 83 corresponds to the number of apertures or couplings 61 associated with the annular ring 51 of the coil former 49. In an embodiment, the number of apertures or couplings 85 corresponds to the number of apertures or couplings 63 associated with the annular ring 51 of the coil former 49. It will be appreciated that any suitable number of apertures or couplings may be used. The coil pack 41 is suspended between the apertures or couplings 83, 85, by interweaving a series of tension members 87, 89 of a high tensile strength, low thermal conductivity material through the apertures or couplings 83, 85. An exemplary material for the tension members 87, 89 is Kevlar. It will be appreciated that other suitable high tensile strength, low thermal conductivity materials may be used.

Tension members 87, 89 suspend the coil former 49 and thereby the superconducting coils 44A-E, 45A-B, 46A-E, 47A-E, 48A-E in close proximity to the walls of the cryostat 43, reducing the potential for coupling vibration into the magnet and minimising the potential for changes in magnet homogeneity during transport.

Cryocooler

Using HTS material means that a highly efficient single stage cryocooler 19 may be used to cool the magnet 7 via conduction instead of the cryogen bath typically required by LTS MRI machines. This may provide several advantages. LTS MRI machines typically use a liquid helium cryostat. A liquid helium cryostat adapted for use with an apparatus having a window would be extremely complex. Liquid helium cryostats are also impractical to move. Cryocoolers are comparatively simple and portable. Use of a cryocooler means the magnet is cryogen-free and can be comparatively easily relocated, and may be used in situations or environments that are not possible for a conventional MRI machine, such as in emergency rooms, mobile neuro-scanning clinics, or other environments.

The cryocooler may be a single stage cryocooler or a two stage cryocooler.

Using a single stage cooler 19, the magnet may have a cool-down time of around one to two days. The magnet 7 using REBCO coils as specified by table 1 will allow the magnet to operate at 30 K. At 30 K during steady-state operation, a single stage cryocooler 19, for example a Cryomech PT63, is able to reject in the order of 10 W of heat load into the magnet cryostat 43.

Imaging Volume

The imaging volume 35 comprises magnetic field variation of more than about 50 ppm peak-to-peak and up to about 1000 ppm peak-to-peak over the imaging volume. In an embodiment, the imaging volume comprises magnetic field variation of more than about 100 ppm peak-to-peak and up to about 1000 ppm peak-to-peak over the imaging volume. In an embodiment, the imaging volume comprises magnetic field variation of more than about 200 ppm peak-to-peak and up to about 1000 ppm peak-to-peak over the imaging volume. In an embodiment, the imaging volume comprises magnetic field variation of more than about 250 ppm peak-to-peak and up to about 1000 ppm peak-to-peak over the imaging volume. In an embodiment, the imaging volume comprises magnetic field variation of more than about 300 ppm peak-to-peak and up to about 1000 ppm peak-to-peak over the imaging volume.

In an embodiment, the imaging volume 35 comprises magnetic field variation of more than about 50 ppm peak-to-peak and up to about 800 ppm peak-to-peak over the imaging volume. In an embodiment, the imaging volume comprises magnetic field variation of more than about 50 ppm peak-to-peak and up to about 600 ppm peak-to-peak over the imaging volume. In an embodiment, the imaging volume comprises magnetic field variation of more than about 50 ppm peak-to-peak and up to about 500 ppm peak-to-peak over the imaging volume. In an embodiment, the imaging volume comprises magnetic field variation of more than about 50 ppm peak-to-peak and up to about 400 ppm peak-to-peak over the imaging volume. In an embodiment, the imaging volume comprises magnetic field variation of more than about 50 ppm peak-to-peak and up to about 350 ppm peak-to-peak over the imaging volume.

The imaging volume 35 is substantially ellipsoidal in shape. In an embodiment, the imaging volume has a length of about 150 mm and a transverse dimension of about 200 mm.

In an embodiment, the imaging volume 35 is slightly larger than half the diameter of the warm bore 26 (375 mm). The ratio of magnet length (about 420 mm) to bore diameter is about 1.1. This ratio is somewhat lower than known magnets that have a minimum ratio of magnet length to bore diameter of approximately 1.2. The magnet 7 achieves a large enough warm bore to allow an operational head-only MRI system, without requiring an excessively large volume of conductor material. This enables the magnet 7 to be cost-effectively produced, and provides a relatively compact and portable magnet.

The magnet 7 is configured to provide an imaging volume 35 that is positioned along a cylindrical axis 29 of the magnet 7 in the recess.

Figure 10:
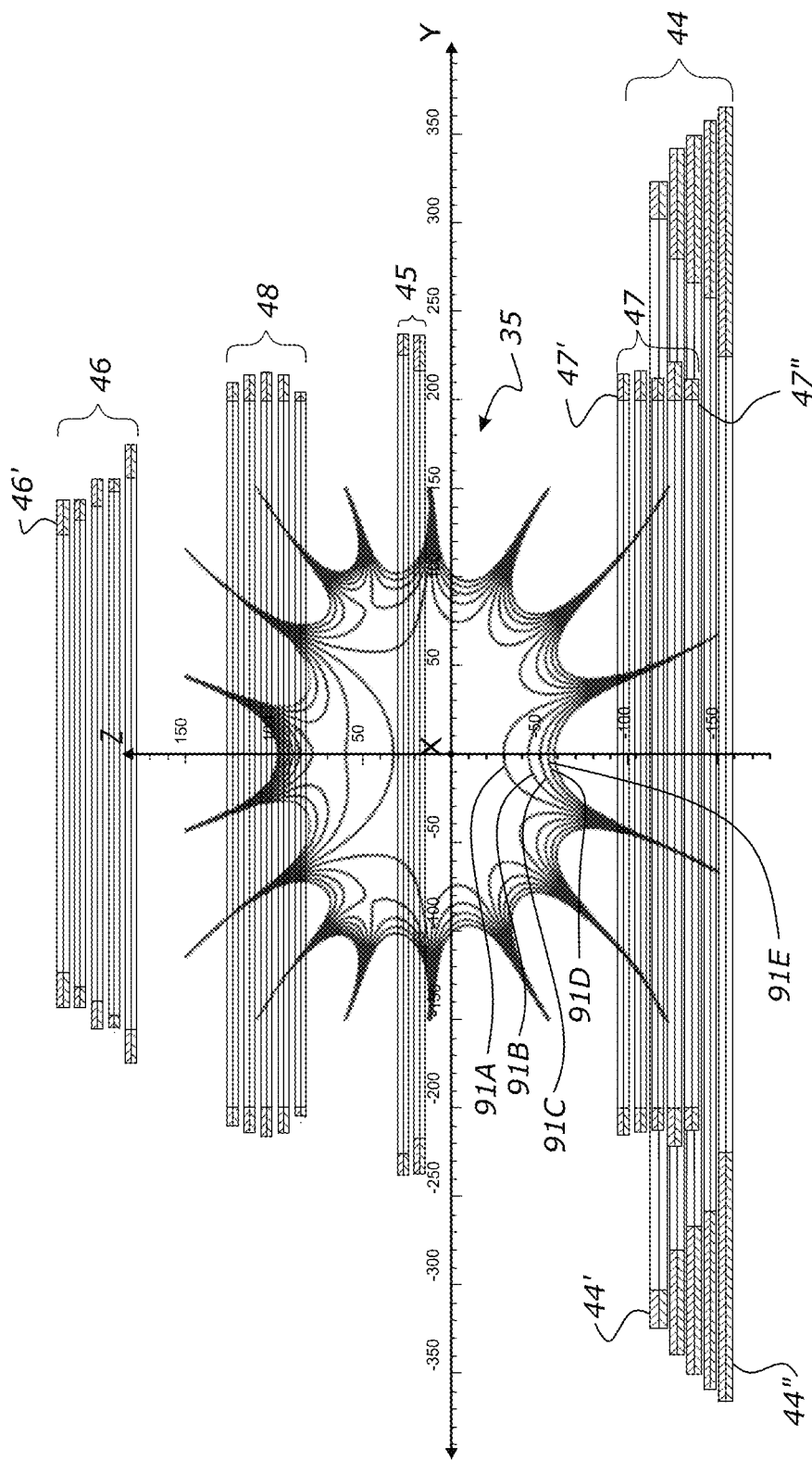
FIG. 10 is a plot of an exemplary imaging volume overlaid on a sectional side view of the exemplary coil arrangement.

FIG. 10 shows a plot of an exemplary imaging volume 35, overlaid on the groups of coils 44, 45, 46, 47, 48 of the exemplary magnet 7. The exemplary imaging volume 35 has a magnetic field variation of 313 ppm peak to peak. This is equivalent to ±10 kHz peak-to-peak field variation in proton-hertz for a 1.5 T magnet. Each field line 91A-E on the plot represents a 2 kHz step in magnetic field variation. The innermost field line 91A represents a region in which there is less than ±2 kHz magnetic field variation. The next field line 91B represents a region in which there is less than ±4 kHz magnetic field variation. The next field line 91C represents a region in which there is less than ±6 kHz magnetic field variation. The next field line 91D represents a region in which there is less than ±8 kHz magnetic field variation. The outermost field line 91E represents a region in which there is less than ±10 kHz magnetic field variation.

Shielding

In an embodiment, the MRI apparatus 1 further comprises magnetic shielding. Magnetic shielding limits the distance the magnetic field extends into the space surrounding the magnet 7. Standard shielding requirements require that no member of the public is exposed to a magnetic field greater than 5 Gauss (0.5 mT) without warning. In practice, the 5 Gauss line of the magnet 7 determines the size of the room that the magnet 7 is installed in. Shielding is advantageous because shielded magnets can be installed in smaller rooms. However, shielding is not essential to the operation of the magnet.

Figure 11:
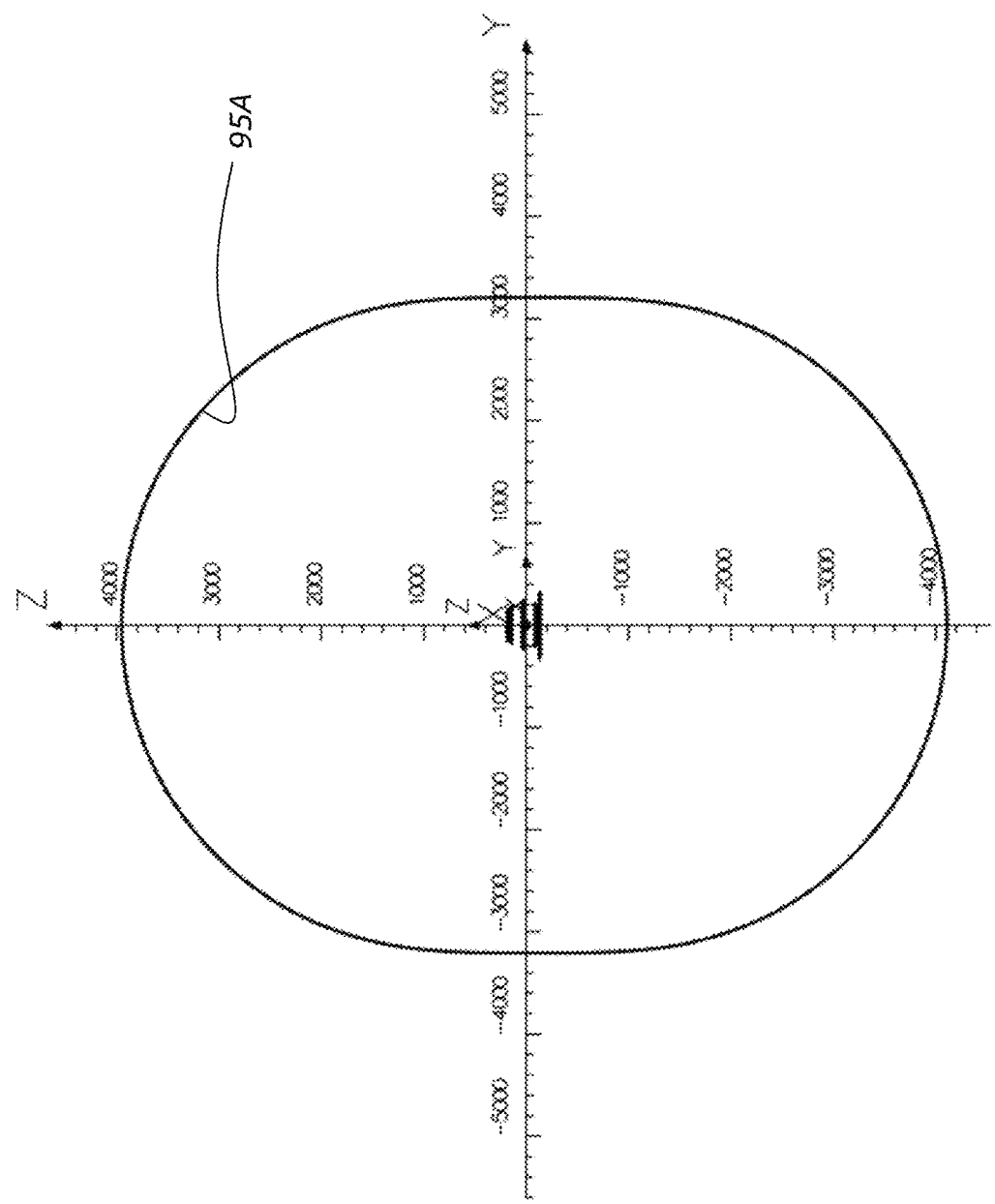
FIG. 11 is a graph that shows the 5 Gauss line corresponding to the unshielded magnet in the Y-Z plane.

FIG. 11 shows the 5 Gauss line 95A corresponding to the unshielded magnet in the Y-Z plane. The 5 Gauss line extends about 3 m from the centre of the magnet 7 in the Y direction and about 4 m from the centre of the magnet 7 in the Z direction.

In an embodiment, the MRI apparatus 1 comprises active magnetic shielding. The active magnetic shielding may comprise further groups of coils (not shown) positioned radially outward of the main groups of coils 44, 45, 46, 47, 48 that generate the main magnetic field in the imaging volume. The further groups of coils are arranged to provide a magnetic field in an opposite sense relative to the groups of coils 44, 45, 46, 48 arranged to provide a magnetic field in the first sense. The further groups of coils act as a return path for the magnetic flux from the magnet 7.

In an embodiment, at least one of the further groups of coils consists of one coil. In an embodiment, all of the further groups of coils each consist of one coil. The coil may comprise LTS material.

In an embodiment, at least one of the further groups of coils consists of a plurality of coils. In an embodiment, all of the further groups of coils each consist of a plurality of coils. The plurality of coils may comprise HTS material.

The further groups of coils may also influence the magnetic field in the imaging volume. It may be necessary to modify the design of the main groups of coils 44, 45, 46, 47, 48 to account for the effect of the further groups of coils in order to achieve the desired field uniformity in the imaging volume.

Figure 12:
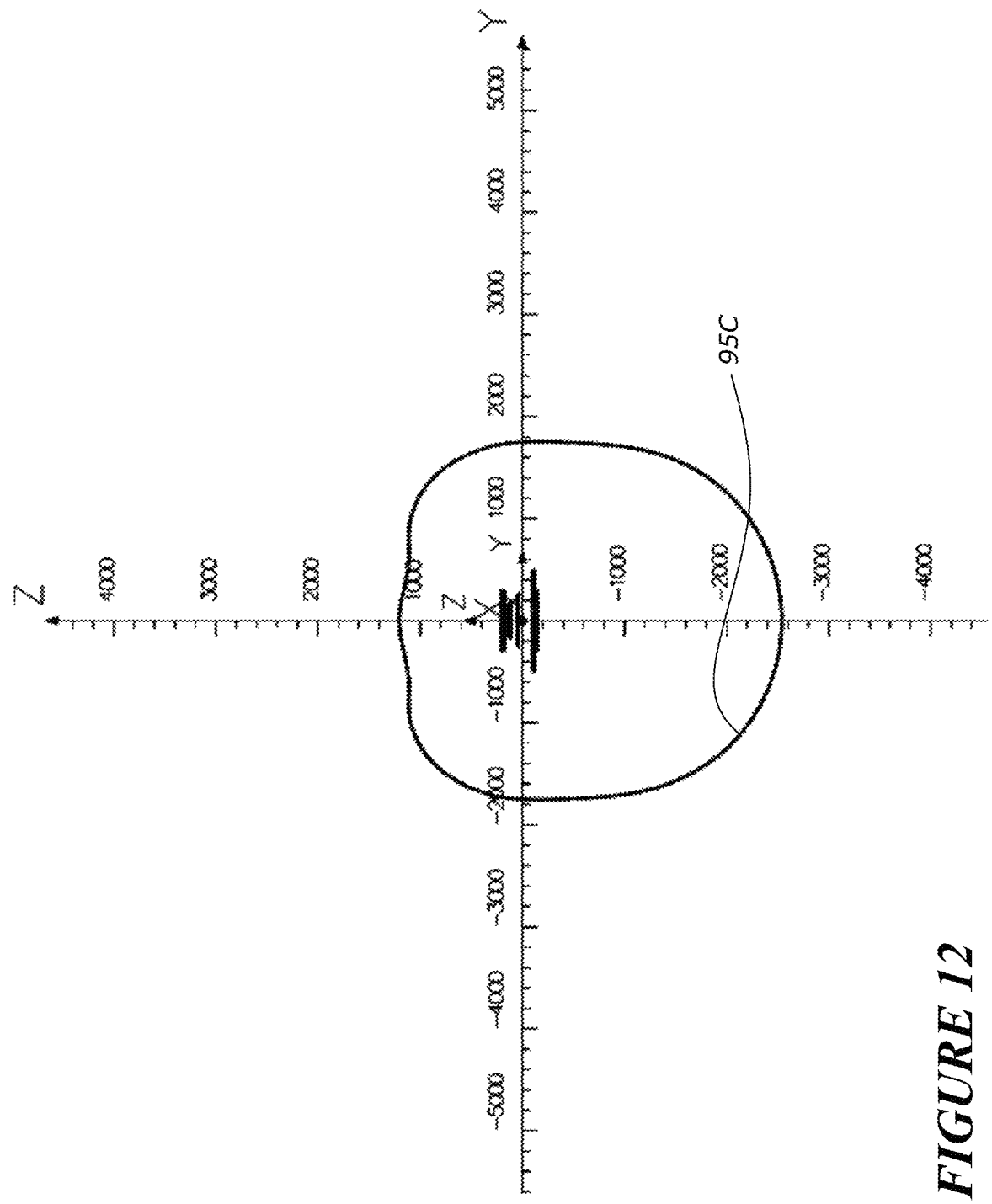
FIG. 12 is a graph that shows the 5 Gauss line corresponding to an actively shielded magnet in the Y-Z plane.

FIG. 12 shows the 5 Gauss line 95C corresponding to an actively shielded magnet 7A. The active shielding reduces the distance that the 5 Gauss line extends from the centre of the actively shielded magnet 7A from about 4 m to about 1 m in the +Z direction and 2.5 m in the −Z direction when compared to the unshielded magnet 7 of FIG. 11. The active shielding reduces the distance that the 5 Gauss line extends from the centre of the actively shielded magnet 7A from about 3 m to about 2 m in the Y direction when compared to the unshielded magnet 7 of FIG. 11.

Alternatively, in an embodiment, the MRI apparatus 1 comprises passive magnetic shielding. The passive shielding may be formed from a steel yoke that surrounds the outside of the magnet 7 to act as a return path for the magnetic flux generated by the magnet 7.

The above description is concerned primarily with the magnet and associated components. It will be understood by those skilled in the art that suitable gradient and radio-frequency coils will also be used with the magnet and associated components to achieve MRI.

Providing of Image—Pulse Sequences

Conventionally, an ultra-short magnet such as the magnet 7 would require an excessive amount of conductor to meet MRI homogeneity requirements (typical limit of around 2 ppm peak-to-peak of field variation). However, with use of pulse sequences such as those described in PCT International Patent Application No. PCT/US2017/056487 (Systems and Methods for Steady-State Echo Magnetic Resonance Imaging), high quality images can be produced with up to around 3000 ppm peak-to-peak of field variation within the imaging volume. Magnet 7 is within acceptable limits for use with both the MP-SSFP and STEREO pulse sequences, both of which have been shown to work in the presence of field variation exceeding 3000 ppm peak-to-peak.

Figure 13:
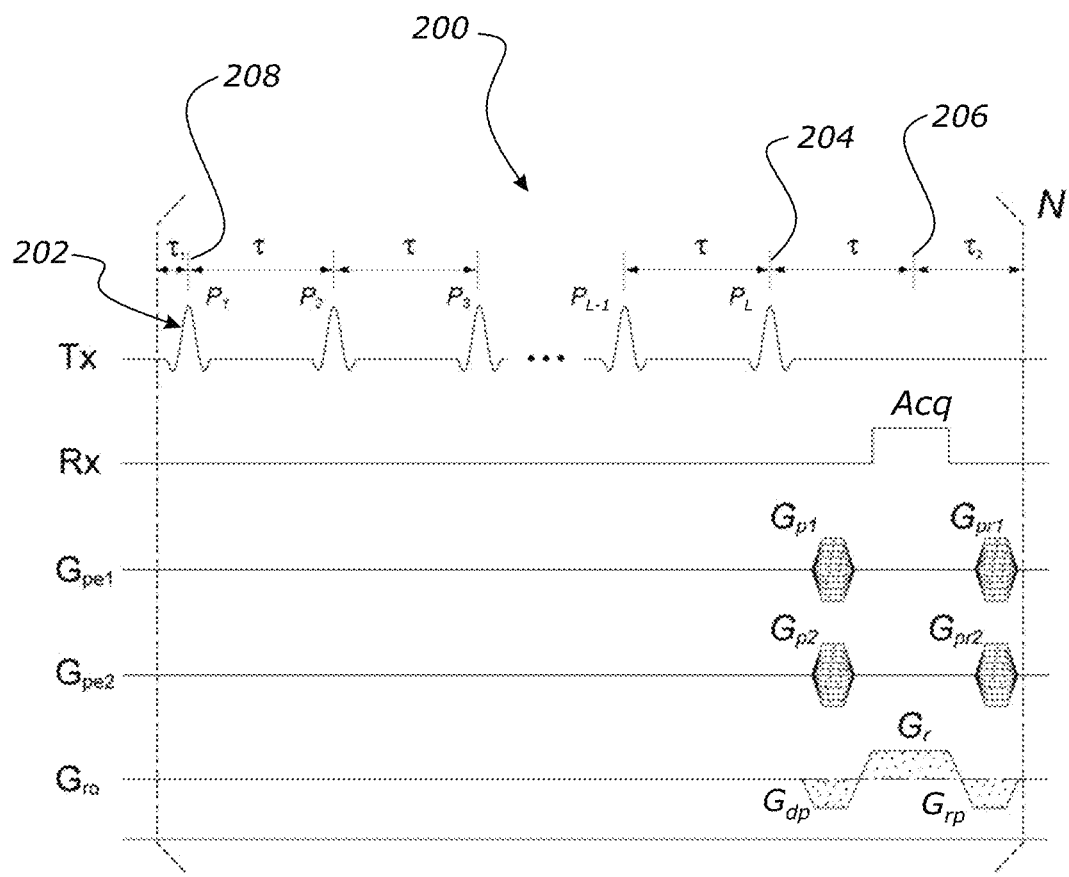
FIG. 13 is a schematic diagram of an exemplary pulse sequence that can be used with the magnet.

Referring to FIG. 13, one non-limiting example of a pulse sequence that can be used with the magnet 7 is shown. In the illustrated pulse sequence 200, spin magnetization can be excited with an RF pulse train 202 under a spatially inhomogeneous magnetic field $\Delta B_0$. In the RF pulse train 202, L individual RF excitation pulses ($P_j$; j=1, 2, . . . L) are applied with a constant time interval, T. The waveform of the RF pulses ($P_j$; j=1, 2, . . . L) in the RF pulse train 202 can be an amplitude modulated pulse (e.g., hard pulse, sinc pulse, Gaussian pulse) or a frequency-modulated pulse (e.g., Chirp pulse, hyperbolic secant pulse). Each of the RF pulses ($P_j$; j=1, 2, . . . L) in the RF pulse train 202 may have a common waveform and pulse duration (pw), but the flip angle ($\alpha_j$) and phase ($p_j$) can be set arbitrarily. The excitation bandwidth (BW) of the RF pulses ($P_j$; j=1, 2, . . . L) depend on the bandwidth of each pulse ($P_j$; j=1, 2, . . . L) in the RF pulse train 202. After the RF pulse train 202, signal acquisition (Acq) is carried out following pulsed phase encoding gradients ($G_{p1}$ and $G_{p2}$).

An RF pulse train 202 of frequency swept RF pulses with relatively small flip angles (FA) can be used. In general, flip angles between 0 degrees to 179 degrees can be used. As one non-limiting example, flip angles between 0.5 degrees and 1.5 degrees can be used.

During signal acquisition (Acq), a pulsed readout gradient field ($G_r$) along with dephasing ($G_{dp}$) and rephasing ($G_{rp}$) gradients before and after the readout gradient ($G_r$) can be optionally applied. Time between the center 204 of the last RF pulse ($P_L$) in the RF pulse train 202 and the center 206 of the signal acquisition window (Acq) is the same as the pulse interval ($\tau$) in the RF pulse train 202.

Following the signal acquisition, phase encode rephasing gradients ($G_{pr1}$, and $G_{pr2}$) are applied to rewind the spin phase introduced by the phase encoding gradients ($G_{p1}$ and $G_{p2}$). That is, the phase encode rephasing gradients ($G_{pr1}$, and $G_{pr2}$) serve the function of a rewinder applied with reverse polarity to ensure stability of the phase of the MR signal in each repetition.

The time between the center 206 of the acquisition window (Acq) and the center 208 of the first RF pulse ($P_1$) in the RF pulse train 202 is equal to the pulse interval ($\tau$) in the RF pulse train 202 (i.e., $\tau_1+\tau_2=\tau$). Therefore, the pulse sequence 200 includes an RF pulse train 202 composed of L+1 RF pulses with a constant interval ($\tau$), where the L+1th pulse can be replaced with data acquisition. Multiple echo acquisition can be conducted by replacing more than one RF pulse with data acquisitions, along with phase encoding and rewinding gradients. Either way, the radio-frequency magnetic field ($B_1$) produced by the RF pulse train 202 is consistent and is sufficient to overcome inconsistencies and inhomogeneities in the $B_0$ field. Generally, L has a value of at least 2, such that echoes refocus at the center of the acquisition window.

The pulse sequence 200 can be repeated N times to acquire refocusing echo signals $S_i$ (i=1, 2, . . . , N) sufficient for 3D image reconstruction by changing the phase encoding gradients ($G_{p1}$ and $G_{p2}$) in successive repetitions. For example, when the phase encoding gradients ($G_{p1}$ and $G_{p2}$) are mutually orthogonal linear gradients in space and applied with constant increments, the number of repetitions, N, is represented by $N=N_{pe1} \times N_{pe2}$, in which $N_{pe1}$ and $N_{pe2}$ are the number of phase encoding steps along the two phase encoding directions. The pulsed readout gradient ($G_r$) and the phase encoding gradients ($G_{p1}$ and $G_{p2}$) can be spatially nonlinear gradients. The increments of phase encoding gradients can be arbitrary.

Other exemplary pulse sequences that can be used include those described in U.S. patent application Ser. No. 13/743,902 (Steering Resonance Along a Trajectory) and U.S. patent application Ser. No. 14/174,368 (Beam Steering With Resonance Along a Trajectory).

All of the above patent applications are incorporated herein in their entirety by way of reference.

In addition to specialist pulse sequences demonstrated to work in non-uniform magnetic fields, such as those described above, it may be possible to use the magnet 7 with conventional pulse sequences that have reasonable tolerance to magnet non-uniformity. Conventional pulse sequences such as spin-echo and fast spin-echo sequences may have sufficient tolerance to a relatively high field variation, allowing them to be used with the magnet 7. It is expected that these conventional MRI pulse sequences, upon post-processing on the basis of a magnet uniformity map, will give good quality MRI images.

Use of the Apparatus

In use of the apparatus 1, the patient P will be positioned in the apparatus 1 so that their head is positioned in the magnet 7 with the centre of their brain aligned with the isocentre 37 and their eyes facing the window 9 so they can see outside the apparatus 1.

The apparatus 1 is then operated to provide MRI images of the patient's brain, via the application of suitable pulse sequences. The images of the patient's brain will be output to a suitable interface such as a display device, storage device, or printer.

The medical provider can interact with the patent visually via the window, or tactilely via the patient's arms or hands which are exposed from the magnet. This also enables the patient to manipulate objects outside the magnet while the brain is imaged.

Providing visual stimulation to the patient enables the brain to be imaged during the visual stimulation, making the apparatus particularly suitable for neural imaging.

A head only MRI apparatus 1 in combination with the compact magnet 7 may overcome many of the disadvantages of known MRI apparatuses. For example, the ability to tolerate relatively high field variation enables the MRI apparatus 1 to have a window 9. The window 9 may reduce the feeling of claustrophobia in patients because it enables a patient to see out of the apparatus 1. The window 9 may also improve communication between a medical provider and a patient because it enables the medical provider to provide visual cues to the patient.

The compact size of the magnet 7 means that the apparatus 1 does not receive the patient's shoulders. Therefore, the patient may retain full use of their arms when their head is received by the apparatus 1.

The compact size of the magnet 7 also enables the apparatus 1 to be more easily transported or moved than conventional MRI apparatuses. The coils also require significantly less superconducting material than conventional MRI apparatuses, so HTS material, which is typically significantly more expensive than LTS material, is a viable option for the superconducting material. If HTS material is used, a cryocooler may be used instead of the cryogen bath typically required for LTS MRI machines, further improving the transportability of the apparatus 1.

The above describes exemplary embodiments of the present invention, and modifications may be made thereto without departing from the scope of the present invention.

For example, where particular configurations, dimensions, and numbers of components are shown, these are exemplary and may be varied without departing from the scope of the present invention.

The invention claimed is:

1. A magnet for use in an apparatus for performing magnetic resonance imaging (MRI) of a patient's head, wherein the magnet is an asymmetric magnet comprising a plurality of superconducting coils that are positioned around a cylindrical axis to provide a magnetic field on the cylindrical axis, the cylindrical axis defining an axial direction of the magnet, wherein the magnet comprises:

a patient end arranged to be positioned adjacent or against a patient's shoulders with the patient's shoulders outside the magnet; and a recess for receipt of the patient's head extending into the magnet from the patient end, wherein the magnet is configured to provide an offset imaging volume in the recess, wherein the imaging volume has an isocentre that is positioned closer to the patient end of the magnet than to the opposite end of the magnet;

wherein the magnet comprises at least three groups of coils in a generally tapering arrangement, with a first group of coils positioned at or toward the patient end having a larger transverse outer dimension than a transverse outer dimension of a second group of coils positioned further from the patient end, and a third group of coils positioned at or toward an opposite end of the magnet having a transverse outer dimension that is smaller than the transverse outer dimension of the second group of coils; and wherein the magnet further comprises an additional group of coils, wherein the first group of coils overlaps the additional group of coils in the axial direction, such that a bottom portion of the additional group of coils is positioned closer to the patient end of the magnet than a top portion of the first group of coils.

2. The magnet according to claim 1, further comprising a fourth group of coils in a generally tapering arrangement with the first, second, and third groups of coils, wherein the fourth group of coils is positioned between the second group of coils and the third group of coils, and wherein the fourth group of coils has a transverse outer dimension that is smaller than the transverse outer dimension of the second group of coils, and larger than the transverse outer dimension of the third group of coils.

3. The magnet according to claim 1, wherein the first, second, and third groups of coils are arranged to provide a summation of magnetic field from the first, second, and third groups of coils and provide a magnetic field in a first sense.

4. The magnet according to claim 2, wherein the first, second, third, and fourth groups of coils are arranged to provide a summation of magnetic field from the first, second, third and fourth groups of coils and provide a magnetic field in a first sense.

5. The magnet according to claim 3, wherein the additional group of coils is arranged to provide a magnetic field in a second sense that is opposite to the first sense.

6. The magnet according to claim 1, wherein the top portion of the first group of coils is positioned closer to the patient end of the magnet than a top portion of the additional group of coils.

7. The magnet according to claim 1, wherein at least the bottom portion of the additional group of coils has a transverse outer dimension that is smaller than a transverse inner dimension of at least the top portion of the first group of coils.

8. The magnet according to claim 1, wherein the magnet is configured to only receive the patient's head and optionally part of the patient's neck, such that the magnet is configured for use as part of a head-only MRI apparatus.

9. The magnet according to claim 1, wherein the magnet defines the cylindrical axis, and the recess and the imaging volume are coaxial with the cylindrical axis.

10. The magnet according to claim 1, wherein the isocentre is positioned between about 130 mm and about 180 mm from the patient end of the magnet, wherein the isocentre is positioned between about 75 mm and about 175 mm above a patient end of the first group of coils, and wherein the isocentre is positioned between about 195 mm and about 240 mm below a top of the third group of coils.

11. The magnet according to claim 1, wherein the imaging volume has a substantially ellipsoidal shape.

12. The magnet according to claim 1, wherein at least one of the groups of coils consists of one coil, wherein said at least one of the groups of coils comprises low temperature superconducting (LTS) material, optionally wherein the coil comprises one of magnesium diboride ($MgB_2$) and niobium tin ($Nb_3Sn$).

13. The magnet according to claim 1, wherein at least one of the groups of coils consists of a plurality of coils, and wherein said at least one of the plurality of coils comprises high temperature superconducting (HTS) material.

14. The magnet according to claim 1, wherein the coils are annular coils that surround the recess and wherein the coils are coaxial with the cylindrical axis.

15. The magnet according to claim 1, wherein the imaging volume comprises magnetic field variation of more than about 50 ppm peak-to-peak and up to about 1000 ppm peak-to-peak over the imaging volume.

16. The magnet according to claim 1, wherein the imaging volume comprises magnetic field variation of more than about 200 ppm peak-to-peak and up to about 500 ppm peak-to-peak over the imaging volume.

17. The magnet according to claim 1, wherein the imaging volume has a length of about 150 mm and a transverse dimension of about 200 mm.

18. The magnet according to claim 1, wherein the magnet further comprises a window to enable a patient to see out of the magnet when their head is positioned in the recess.

19. The magnet according to claim 18, wherein the window is positioned between the second group of coils and the additional group of coils.

20. An MRI apparatus for imaging a patient's head, the MRI apparatus comprising the magnet according to claim 1, wherein the MRI apparatus is a head-only MRI apparatus.

* * * * *